(12) United States Patent
Bogner et al.

(10) Patent No.: US 7,892,492 B2
(45) Date of Patent: Feb. 22, 2011

(54) FLOW-THROUGH APPARATUS FOR MICROSCOPIC INVESTIGATION OF DISSOLUTION OF PHARMACEUTICAL SOLIDS

(75) Inventors: Robin H. Bogner, Hampton, CT (US); Theodore L. Bergman, Storrs, CT (US); Kristyn Greco, Mansfield Center, CT (US); Derek J. Michaels, Windham, NH (US); Szymon J. Chawarski, New Haven, CT (US)

(73) Assignee: University of Connecticut, Farmington, CT (US)

( * ) Notice: Subject to any disclaimer, the term of this patent is extended or adjusted under 35 U.S.C. 154(b) by 724 days.

(21) Appl. No.: 11/635,312

(22) Filed: Dec. 7, 2006

(65) Prior Publication Data

US 2008/0138261 A1 Jun. 12, 2008

(51) Int. Cl.
| | |
|---|---|
| G01N 15/06 | (2006.01) |
| G01N 1/10 | (2006.01) |
| B01L 3/00 | (2006.01) |
| B01L 99/00 | (2010.01) |
| B01L 9/00 | (2006.01) |
| B01D 11/04 | (2006.01) |
| B01D 11/02 | (2006.01) |

(52) U.S. Cl. .......... 422/68.1; 422/99; 422/101; 422/102; 422/104; 422/266; 422/255; 356/246

(58) Field of Classification Search .......... 422/266, 422/255, 68.1; 356/246
See application file for complete search history.

(56) References Cited

U.S. PATENT DOCUMENTS 7,024,955 B2   4/2006   Carlson et al.

| | | | |
|---|---|---|---|
| 2004/0017884 A1 | 1/2004 | Havrilla et al. | |
| 2005/0121604 A1* | 6/2005 | Mueth et al. | 250/251 |
| 2005/0214847 A1 | 9/2005 | Havrilla et al. | |
| 2005/0266582 A1* | 12/2005 | Modlin et al. | 436/164 |

(Continued)

OTHER PUBLICATIONS

'The insertion cell': A novel approach to monitor drug release from semi-solid dosage forms, International Journal of Pharmaceutics, vol. 133, Issues 1-2, May 14, 1996, pp. 59-63, S. C. Chattaraj, I. Kanfer.*

(Continued)

*Primary Examiner*—Jill Warden
*Assistant Examiner*—Dean Kwak
(74) *Attorney, Agent, or Firm*—McCarter & English, LLP

(57) ABSTRACT

The present disclosure is directed to an apparatus and method for studying dissolution of a compact sample. The compact sample is typically a pharmaceutical drug sample. A flow-through apparatus includes a frame defining a flow-through channel, a removable insert having a drug sample, the insert positioned within the frame such that a fluid interacts with the sample when the fluid passes through the flow channel. The frame has an opening on the top side to allow a glass plate, typically a microscope cover slip to be positioned within the frame and allow viewing of the fluid flow and interaction with the drug sample. The hydrodynamics of the fluid flow are either known or computed. Thus, dissolution can be studied and observed in view of hydrodynamic characteristics. Typically, only a small amount of sample is necessary for a study. The flow-through apparatus is designed to fit on a microscopy stage and allow visual observation of the fluid/sample interaction.

27 Claims, 18 Drawing Sheets

U.S. PATENT DOCUMENTS

2007/0003008 A1    1/2007    Warner et al.

OTHER PUBLICATIONS

Release of acyclovir from semi-solid dosage forms: A semi-automated procedure using a simple plexiglass flow-through cell, International Journal of Pharmaceutics, vol. 125, Issue 2, Oct. 31, 1995, pp. 215-222, S. C. Chattaraj, I. Kanfer.*

V. Levich, Physicochemical Hydrodynamics, Convection Diffusion in Liquids, Prentice-Hall, Englewood Cliffs, Table of Contents and pp. 60-73, 1962.

A. C. Shah, et al.; Evaluation of a Convective Diffusion Drug Dissolution Rate Model, Journal of Pharmaceutical Sciences, vol. 64, pp. 1518-1520 (1975).

W.C.G. Butler, et al.. A Flow-Through Dissolution Method for A Two Component Drug Formulation Where The Actives Have Markedly Differing Solubility Properties, Internationl Journal of Pharmaceutics, vol. 173: pp. 211-219 (1998).

L. Peltonen, et al., Dissolution Testing of Acetylsalicyclic Acid By A Channel Flow Method-Correlation to USP Basket And Intrinsic Dissolution Methods, European Journal of Pharmaceutical Sciences Sheet, vol. 19: pp. 395-401 (2003).

W. Sun, et al., A Mechanistic Study of Danazol Dissolution in Ionic Surfactant Solutions, Journal of Pharmaceutical Sciences, vol. 92: pp. 424-435 (2003).

J. Van Der Weerd, et al., An innovative Design of Compaction Cell for in Situ FT-IR Imaging of Tablet Dissolution. Vibrational Spectroscopy, vol. 35: pp. 9-13 (2004).

J. Van Der Weerd and S.G. Kazarian. Combined approach of FTIR imaging and conventional dissolution tests applied to druge release. Journal of Controlled Release, vol. 98, pp. 295-305 (2004).

L. Peltonen, et al., A Novel Channel Flow Method in Determination Of Solubility Properties And Dissolution Profiles of Theophylline Tablets, Journal of Drug Delivery Science and Technology vol. 14: pp. 389-394 (2004).

A. C. Shah and K. G. Nelson, *Evaluation of a convective diffusion drug dissolution rate model*, Journal of Pharmaceutical Sciences, 64: 1518-20 (1975).

* cited by examiner

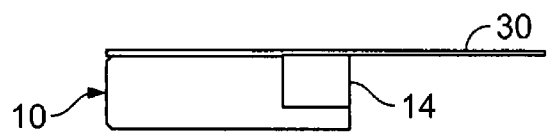
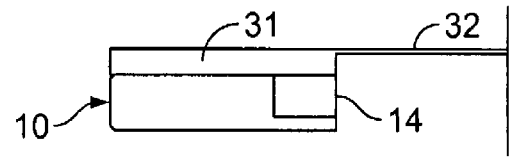
FIG. 3A        FIG. 3B
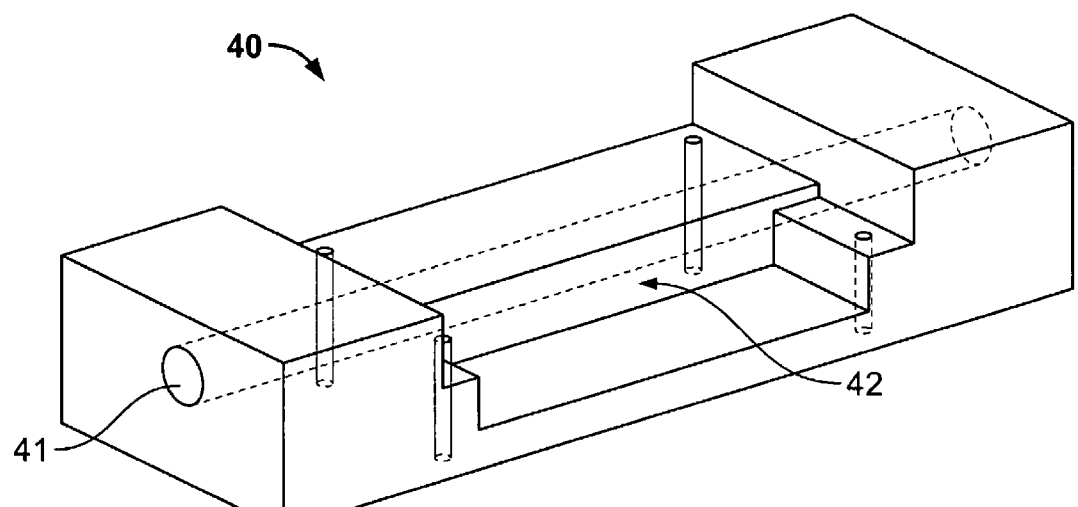
FIG. 4

US 7,892,492 B2

FLOW-THROUGH APPARATUS FOR MICROSCOPIC INVESTIGATION OF DISSOLUTION OF PHARMACEUTICAL SOLIDS

BACKGROUND

1. Technical Field

The present disclosure relates to systems and methods for investigating dissolution of pharmaceutical solids.

2. Background Art

Dissolution of a drug from the solid state in a solid oral dosage form is a key step in the absorption and eventual therapeutic effect of a drug. Once a potential drug has been identified, a proper solid form (e.g., polymorph, salt form) must be chosen. In choosing a proper solid form, certain behavioral properties must be taken into consideration such as, for example, dissolution rates, equilibrium solubility, physical and chemical stability. Dissolution rates depend on the hydrodynamics of the fluid adjacent to the solid state drug. Hydrodynamics of most standard dissolution test methods are not fully understood.

Lack of hydrodynamic data makes studying the hydrodynamic impact on any interesting phenomena that could arise (e.g., salt form changes, polymorph changes) challenging in predicting bioavailability in humans. For example, using current systems/methods, when unexpected change in dissolution rates during standard testing occurs, typically an analyst cannot easily observe physical changes in real time associated with changes in dissolution. Also, current dissolution testing systems/methods require large amounts of test sample. This creates a serious burden on a typical research analyst or research group since they may receive only a few milligrams of a new compound designated to undergo several tests.

There are many dissolution methods currently used for characterizing pharmaceutical solids. Standard USP (United States Pharmacopoeia) methods include USP Type I, II and IV. The USP Type I method is commonly known as the basket method, in which the tablet is placed in a basket that is rotated in a fixed volume bath of dissolution medium. USP Type II method is commonly known as the paddle method in which the solid is placed at the bottom of the dissolution bath while a paddle agitator aids in dissolution. USP Type IV method is a flow-through device in which the solution flows through a cell in which the solid is suspended. These standard methods, however, fail to appreciate or consider the exact hydrodynamics since the fluid flow characteristics are complicated and time dependent.

Currently, other non-USP methods include Wood's die apparatus, and various flow-through devices found in pharmaceutical literature. The Wood's die apparatus is a rotating device in which the solid test sample is compressed such that the surface area of the solid remains constant. The device is placed in a dissolution bath and allowed to rotate. The hydrodynamics of this system have been thoroughly described by Levich. (See, e.g., V. Levich. *Physicochemical Hydrodynamics*, Prentice-Hall, Englewood Cliffs, 1962.) In 1975 Nelson and Shah described a flow cell in which a pharmaceutical sample was compressed and fluid was allowed to flow over the top of the compressed pharmaceutical. (See, e.g., A. C. Shah and K. G. Nelson, Evaluation of a convective diffusion drug dissolution rate model, *Journal of Pharmaceutical Sciences* 64: 1518-20 (1975)). The hydrodynamics of this system have been described along with similar flow though devices by other authors including Sun and Missel. (See, e.g., W. Sun, C. K. Larive and M. Z. Southard, A mechanistic study of danazol dissolution in ionic surfactant solutions, *Journal of Pharmaceutical Sciences* 92: 424-435 (2003); and P. J. Missel, L. E. Stevens and J. W. Mauger. Reexamination of convective diffusion/drug dissolution in a laminar flow channel: Accurate prediction of dissolution rate. *Pharmaceutical Research* 21: 2300-2306 (2004)). In each of the aforementioned descriptions, whether the hydrodynamics are fully understood or not, none describes a system capable of visualizing the pharmaceutical solid during dissolution.

Visualization is a critical aspect to gaining a thorough understanding of the dissolution process, particularly if the solid undergoes some kind of transition such as, for example, polymorph change, amorphous to crystalline transition, or a salt form conversion. One flow cell apparatus/method described by Van Der Weerd, does allow for visualization of the tablet during dissolution by FTIR imaging. (See, J. van der Weerd, K. L. A. Chan and S. G. Kazarian, An innovative design of compaction cell for in situ FTIR imaging of tablet dissolution, Vibrational Spectroscopy 35: 9-13 (2004); J. van der Weerd and S. G. Kazarian, Combined approach of FTIR imaging and conventional dissolution tests applied to drug release, Journal of Controlled Release 98: 295-305 (2004); and J. Van Der Weerd and S. G. Kazarian, Release of poorly soluble drugs from HPMC tablets studied by FTIR imaging and flow-through dissolution tests, Journal of Pharmaceutical Sciences 94: 2096-2109 (2005)). While visualization is possible using the aforementioned systems/methods, the disclosed systems/techniques fail to appreciate or consider complete characterization of the hydrodynamics of the system. Similarly, various techniques have been described for a flow-through dissolution apparatus that inadequately address hydrodynamics. (See, e.g., W. C. G. Butler and S. R. Bateman, A flow-through dissolution method for a two component drug formulation where the actives have markedly differing solubility properties, International Journal of Pharmaceutics 173: 211-219 (1998); L. Peltonen, P. Liljeroth, T. Heikkila, K. Kontturi and J. Hirvonen, Dissolution testing of acetylsalicylic acid by a channel flow method-correlation to USP basket and intrinsic dissolution methods, European Journal of Pharmaceutical Sciences 19: 395-401 (2003); E. D. Carlson, M. Petro and S. H. Nguyen, Methods and systems for dissolution testing, and use in drug candidate evaluation, U.S. Pat. Appl. Publ., (USA). Us, 2004, pp. 37; G. J. Havrilla, T. C. Miller, B. P. Warner, C. L. Lewis, C. A. Mahanand, and C. A. Wells, Flow method and apparatus for screening chemicals using micro x-ray fluorescence, U.S. Pat. Appl. Publ., (USA) Us, 2004, pp. 9; and L. Peltonen, P. Liljeroth, T. Heikkila, K. Kontturi and J. Hirvonen, A novel channel flow method in determination of solubility properties and dissolution profiles of theophylline tablets, Journal of Drug Delivery Science and Technology 14: 389-394 (2004).)

Salt selection is an important component of the drug development process. Effective salt selection can lead to a significant increase in solubility over free base/free acid form, which may result in superior bioavailability. The solubility advantage and expected increase in bioavailability are often lost upon the conversion of the salt form to a less soluble form, including the sparingly soluble free acid/base form. When choosing a salt form, aqueous solubility alone is not enough information to understand the full solubility advantage of a salt form due to the propensity to convert to a lower solubility form during solubility studies. To fully understand the potential in vivo performance of a selected sample, the salt solubility, dissolution rate, conversion rate and precipitation at multiple pH values of a given sample should be explored. By studying the combination of solubility, dissolution, conversion and precipitation effects, bioavailability of salt forms can be better predicted.

It is commonly known that highly soluble salts of basic drugs are prone to conversion to the HCl salt in the stomach which has a lower solubility due to common ion effect. In the intestines, due to the increased pH, salts of basic drugs can undergo a conversion to the sparingly soluble free base form. It is of general interest to determine how and when these conversions occur and if they occur on a time scale relative to absorption. Currently, the conditions under which these phenomena should be optimally studied are not fully understood. Knowledge of hydrodynamic conditions during dissolution is paramount to studying these effects due to the combination of mass and momentum transport coupled with reactive dissolution that occurs.

The hydrodynamics of most standard pharmaceutical dissolution test methods are not fully understood, which makes studying the hydrodynamic impact on any interesting phenomena that could arise (e.g., salt form changes, polymorph changes) nearly impossible. When there is an unexpected change in dissolution rates during standard testing, the scientist cannot easily observe any visual changes that accompany such a change. More importantly, currently available standard methods require a large amount of material. With the advancements made in high throughput screening, dissolution testing should ideally be studied early in the development process using very little solid.

These and other disadvantages and/or limitations are addressed and/or overcome by the systems and methods of the present disclosure.

SUMMARY

The present disclosure describes systems and methods for measuring and observing a pharmaceutical sample interacting with fluid flow. In an exemplary embodiment, a flow-through apparatus associated with the present disclosure includes a frame defining at least one flow-through channel adapted to allow a fluid to pass through the frame, a removable insert positioned within the frame defining a cavity adapted to receive a compact sample, and at least one glass plate positioned within the frame above the insert. The frame includes a top portion and a bottom portion adapted to fit securely one on top of the other, each defining an opening substantially within the center of the top portion and bottom portion. The insert is positioned within the frame to create a space for the flow-through channel to allow fluid to pass through the frame. The glass plate is adapted to fit securely within the frame and allow visualization of the fluid passing through the flow channel.

In an exemplary embodiment, the compact sample is a pharmaceutical sample adapted to be compacted within the cavity of the insert. Although reference is made to a pharmaceutical sample, it is noted that the compact sample may be any solid form substance in which the dissolution properties are of interest to study. An exemplary frame associated with the present disclosure is substantially rectangular and the flow-through channel is defined along the elongated axis of the frame. The insert is substantially rectangular in shape and the defined cavity is adapted to receive the compact sample such that the compact sample is compacted into a shape adapted to define at least one substantially planar face. The planar face should be adapted to allow fluid to interact such that dissolving properties are visually observable. In an exemplary embodiment, the compact sample is substantially a three dimensional rectangle and the dimensions of the sample compacted into the cavity are 2 mm in height, 4 mm in width, and 1-2 mm in thickness. An exemplary apparatus associated with the present disclosure may have dimensions of 75 mm in length, 40 mm in width, and 1.5 cm in height.

In an exemplary embodiment, the defined flow-through channel is substantially rectangular. Dimensions of a perpendicular cross section of the flow-through channel may be selected from dimensional combinations such as but not limited to: 2×4 mm, 4×4 mm, and 6×2 mm. Typically, the compact sample compacted within the cavity defines three exposed substantially planar faces. Accordingly, the insert is positioned within the frame such that the fluid interacts with an exposed face of the compact sample as it passes through the frame. At least one of the other two exposed faces is visible through the glass plate positioned within the top portion of the frame. In an exemplary embodiment, all three exposed faces are visible through the at least one glass plate positioned within the top portion of the frame. The interaction of the fluid with one of the exposed faces of the compact sample may be observable through a microscopy means.

In an exemplary apparatus associated with the present disclosure, the frame further includes a second glass plate positioned to space the sample away from the first glass plate that covers the flow-through channel. Typically, at least one of the glass plates are microscope coverslips that securely fit within the frame and adapted to cover a custom cut glass plate over the compact sample and the flow-through channel. The frame is typically adapted to fit on a microscope stage. Typically, the frame and insert are fabricated from stainless steel. In an exemplary embodiment, the apparatus can include a flow guide block adapted to guide fluid flow through the flow channel. The flow guide block is typically made of steel.

The fluid is typically pumped into the flow-through channel by a fluid delivery means. In an exemplary embodiment, the fluid delivery means is a syringe pump. The hydrodynamic characteristics of the fluid flow through the flow-through channel are generally known or computed. Typically, the fluid flow through the flow channel is laminar.

The present disclosure further relates to a method for studying dissolution of a pharmaceutical sample including: (a) compacting a pharmaceutical sample into a cavity defined on a side of a removable insert such that the compact defines at least one substantially planar face exposed to fluid flowing through a flow channel; (b) positioning the insert within a frame having a top and bottom portion wherein at least the top or bottom portion defines an opening adapted to receive a glass plate and the frame defines the flow-through channel adapted to allow fluid to pass through the frame; and (c) pumping the fluid through the flow-through channel such that the fluid interacts with the at least one exposed planar face of the compact. In an exemplary method, the interaction of the fluid and the compact sample is visible through the glass plate. In an exemplary embodiment, a flow guide block is positioned within the frame such that a space is provided to allow the fluid to pass through the flow-through channel. Dissolution of the compacted sample is thus measurable and/or observable.

In an exemplary embodiment, a cross section of the flow-through channel is substantially rectangular in shape. A method according to the present disclosure describes the frame to be adapted to fit on a microscopy stage, thereby allowing the interaction of the fluid with the compacted sample to be observed with a microscopy means. An exemplary compacted sample is substantially shaped into a three dimensional rectangle. The hydrodynamic characteristics of the fluid flow through the flow channel are generally measurable and/or known. Typically, the fluid flow through the flow channel is laminar. The frame, insert and flow guide block are fabricated from stainless steel.

Additional features, functions and benefits of the disclosed systems and methods will be apparent from the description which follows, particularly when read in conjunction with the appended figures.

BRIEF DESCRIPTION OF THE DRAWINGS

To assist those of ordinary skill in the art in making and using the disclosed systems and methods, reference is made to the appended figures, wherein:

FIG. 3(a) illustrates a cross sectional view of an exemplary insert with a compact sample and a glass cover;

FIG. 3(b) illustrates a cross sectional view of an exemplary insert with a compact sample, a glass cover and a glass spacer plate;

FIG. 4 illustrates an exemplary flow-through apparatus made of plastic associated with the present disclosure;

DESCRIPTION OF EXEMPLARY EMBODIMENT(S)

Figure 1:
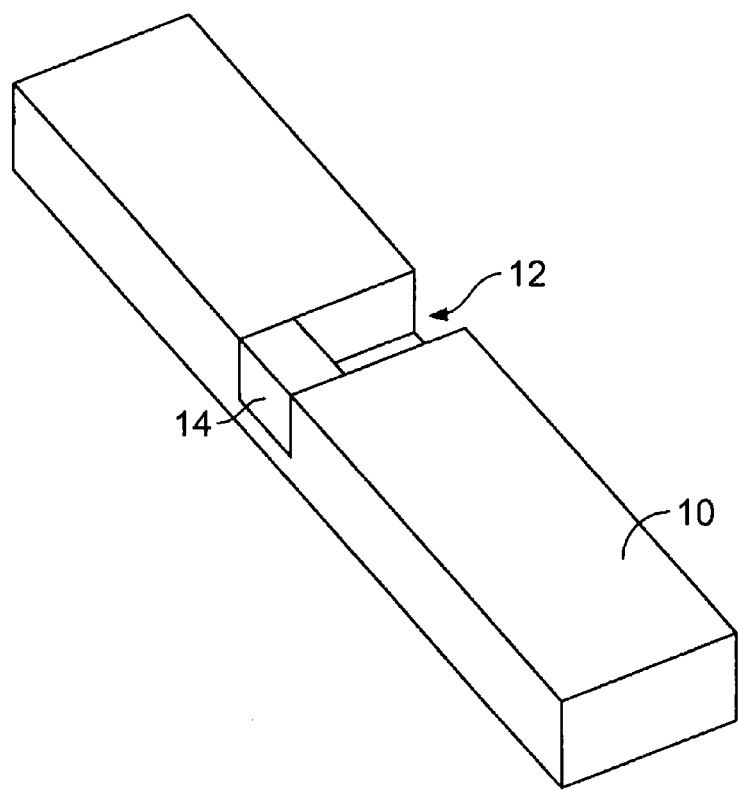
FIG. 1 illustrates an exemplary removable insert with a compact sample.

The present disclosure relates to a flow-through dissolution apparatus that is typically designed such that the flow pattern is uncomplicated and the velocity profile is well-characterized. Knowledge of the velocity profile can be used with mass transfer equations to fully describe the dissolution process. An exemplary flow-through apparatus associated with the present disclosures allows for improved understanding of mass transfer characteristics of a particular drug from the solid surface (i.e. dissolution) and both convective and diffusion components. An exemplary dissolution flow cell associated with the present disclosure can be designed to fit on a microscope stage. A particular aspect of the present disclosure allows a user (i.e., a scientist or a research analyst) to view a solid sample, such as a drug, through a glass window while only using a relatively small sample size.

Typically, a pharmaceutical solid is compressed in an exemplary dissolution apparatus and fluid is allowed to pass by one face of the solid so that both the dry and dissolving portions of the solid are observable using a means of microscopy (e.g., Raman, confocal fluorescence, FTIR, brightfield, polarizing light, etc). The apparatus generally allows a user to observe the solid and liquid during dissolution, particularly when the pharmaceutical solid undergoes some type of transition and/or unusual behavior. Exemplary transitions of interest include, but are not limited to: (1) conversion of one salt form to another; (2) conversion of a salt to free acid or free base; (3) amorphous to crystalline form; (4) anhydrous to hydrate, (5) visualization of solution conditions (e.g., pH in particular) in the solution adjacent to the dissolving solid, (6) screening of inhibitors of solvent-mediated conversion, and (7) screening a formulated solids for inhibition of solvent-mediated conversion. It is a further aspect of the present disclosure that by fully understanding the mass transfer of a particular system, hydrodynamic impact on observed transitions can be better understood. With a thorough understanding of hydrodynamic effect on solid transitions, the ability to predict the bioavailability of a particular drug is enhanced. Moreover, a better understanding may lead to enhancements that may be achieved by manipulating the solid form of a particular drug, thereby reducing the number of animal and/or human studies previously required and significantly reducing time to market for many pharmaceutical products.

The present disclosure describes systems/methods that facilitate evaluation and/or viewing of the hydrodynamics of an exemplary dissolution process as well as allowing for visualization of a solid sample during dissolution, while minimizing quantity of sample material. In an exemplary embodiment, a device is designed such that the flow regime is laminar, thus allowing for the velocity profile to be fully described by computational fluid dynamics for a wide range of flow rates. This particular exemplary device can also be designed in such a way that it will fit on a microscope stage. A particular pharmaceutical solid sample is easily viewed through a glass window allowing for relevant phenomena to be observed and characterized through analytical microscopy and/or image analysis. Typically, visibility is achieved by allowing only one face of a solid sample to be exposed to a dissolution medium so the remaining solid can be used as a real-time control sample (i.e., remaining solid). A system/method associated with the present disclosure allows for observation of changes occurring on the face of a solid sample when fluid flows by the solid sample.

An exemplary flow-through dissolution cell associated with the present disclosure is capable of facilitating evaluation and/or study of dissolution under well defined hydrodynamic conditions and local concentrations, thereby facilitating an understanding of complications due to fluid flow and local concentrations of a drug and other species in a system in which salt conversion occurs. The following examples are meant to more clearly describe and illustrate the present disclosure and in no way are intended to limit the disclosure thereto.

An exemplary flow cell was fabricated with the aid of computational fluid dynamics to fully understand the hydrodynamics during dissolution and tested using a sparingly soluble basic drug. The dissolution rate of Triamterene free base in the disclosed flow cell was compared to the dissolution rate in a Wood's die apparatus as well as literature data associated with currently existing dissolution apparatus. Flow cell and flow-through apparatus are interchangeable terms and will be used interchangeably throughout the disclosure. A comparison between a flow cell associated with the present disclosure and Wood's die apparatus on the conversion of Triamterene citrate to hydrochloride salt is described herein.

Objectives associated with the present flow cell design included: (1) decreasing sample size necessary to perform a study to about 50 mg or less; (2) allowing for real-time visual or microscopic inspection of changes in a sample; and (3) allowing for a range of fully characterized hydrodynamic conditions at which a dissolution rate can be measured.

An exemplary flow cell according to the present disclosure has the following characteristics:

1) Requires a small sample size (50 mg or less); an exemplary flow cell is capable of studying 15 mg of sample;

2) The flow cell is small enough to fit on a microscope stage; both the dry and dissolving portions of the solid are observable using a microscopy means; this allows the dry portion to act as a real time control for the converting solid; and 3) The flow pattern and mass transport associated with the flow cell can be described by differential equations that can be solved either with computational fluid dynamics (CFD) or analytically to fully describe the dissolution process; this allows testing dissolution rates in steady, fully-developed, laminar flow; typically, the surface area remains constant during dissolution, thus not requiring to take into account contracting geometry, i.e., simplifying the boundary conditions.

Typically, a drug compact sample is directly observable when placed in a flow channel having optically transparent walls. An exemplary system/method associated with the present disclosure ensures that a drug sample is flush with one of the walls of the flow channel, thus reducing eddy effects and complicated flow patterns.

Currently existing testing systems/methods, such as the Wood's die, require a drug sample to be compacted into a die and remain in this die during dissolution. The compacting process typically uses a pneumatic press that applies approximately 283,000 kPa of pressure over 30 seconds to compress the drug into its die. The present disclosure describes systems/methods in which the drug is compacted into a small insert that can be moved from a pneumatic press and inserted directly into an exemplary testing flow cell.

Referring again to the Wood's die apparatus, the die used is typically cylindrical defining a round hole through its center. The die is bolted onto a flat surface and the powder form of the drug is placed into the hole. A plunger is then inserted into the hole and pressure is applied until the drug is compacted. The result of this process is that the drug is firmly secured in the die and that the exposed face is flush with the face of the die. This compacting process requires that at least two faces (the exposed face and the back face) of the pharmaceutical sample, once compacted, be planar.

An advantageous aspect of a flow cell associated with the present disclosure is that one face of the sample drug (typically the sample is compacted into a generally three dimensional rectangular geometry) is perpendicular to the dissolving face (the face that is exposed to the fluid flow) and is externally visible. Once the solid sample is compacted, three faces of the compacted sample will be considered open (i.e., the face exposed to flow, the visible adjacent face, and the back face to which pressure is applied, typically by a plunger means).

In an exemplary implementation, to reduce the sample size, the compact surface area exposed to the fluid is 2×4 mm having a thickness of 1-2 mm. The compact mass, based on the above dimensions, is typically around 15 mg, significantly lower than 50 mg. Typically, at least one face of the compact is substantially planar and adapted to allow fluid to interact with sample on the planer face such that dissolving characteristics may be visually observed. In an exemplary embodiment, a compact sample according to the present disclosure is compacted into the cavity of the insert such that it defines a substantially three-dimensional rectangular geometry. In an exemplary embodiment, a system includes a removable insert in which the drug is compressed and then the entire insert is placed in a flow cell. FIG. 1 illustrates an exemplary insert 10 defining a cavity 12 adapted to receive a material sample 14 capable of being compacted by a compacting means. Typically sample 14 is a pharmaceutical sample.

In a Wood's die apparatus, drugs are pressed into a die with 283,000 kPa of pressure. This requires 22 kN of force, which is applied with a pneumatically activated vice. Typically, the applied force can be varied from 2 kN to 22 kN. In an exemplary flow cell apparatus of the present disclosure, a removable insert 10 is adapted to receive a plunger 16, shown in FIG. 2 (essentially a rectangular block). In an exemplary embodiment, the plunger can be designed to be adapted to left in place to provide mechanical support for small sample quantities. Plunger 16 can be, for example, AISI 302 steel, which typically has a yield strength of 861,000 kPa. About 150 mg of a sample drug is used to create the cylindrical compact in a Wood's die, which typically measures 1 cm in diameter and approximately 2 mm in thickness. In an exemplary flow cell associated with the present disclosure, compact 14 is significantly smaller. For example, compact 14 can measure 2 mm in height, 4 mm in width, and 1-2 mm in thickness. The resulting cross sectional area of compact 14 is significantly smaller than the cylindrical sample used in a Wood's die apparatus, and therefore the necessary force to compact it to 283,000 kPa is much lower.

Figure 2:
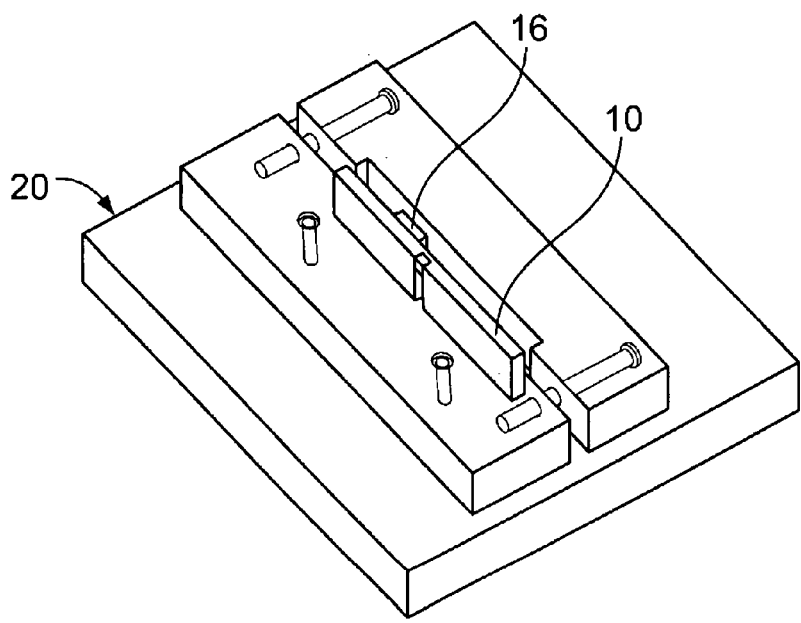
FIG. 2 illustrates a compaction device with plunger and an exemplary removable insert.

Referring again to the exemplary flow cell associated with the present disclosure, using a cross sectional area of 8 $mm^2$, a force of 2.25 kN is required to compress compact 14 to 283,000 kPa. Referring to FIG. 2, insert 10 is placed into a compaction device 20. The required pressure to compact the sample is significantly lower than the yield stress of the steel. Based on the yield stress of the 302 steel, a force of 6.9 kN could be applied before plunger 16 would fail due to yielding.

Since compact sample 14 defines a substantially planar face, a flow channel defined within a frame according to the present disclosure defines at least one planar flow path adapted to allow fluid to interact with the planar face of the sample. In an exemplary embodiment, compact sample 14 defines a substantially three-dimensional rectangular geometry having at least one planar face exposed to the flow. Typically, the flow channel is adapted to have a substantially rectangular cross section. A limiting feature to using a rectangular as opposed to a round cross-section is that there can be corner effects generated along the edges. In order to minimize the effect of flow in the corners on a compact sample 14, it is advantageous to place sample 14 away from the corners of the channel. FIG. 3(a) illustrates a cross section view of the interface between a glass cover 30 and compact sample 14, compacted within insert 10. In an exemplary embodiment shown in FIG. 3(b), two glass plates 31 and 32 are covering compact sample 14, one that covers the channel and one that spaces sample 14 away from a corner. The thickness of plates 30 and 32 should be made as small as possible. Plate 31 should have a defined thickness adapted to minimize corner effects.

In an exemplary embodiment, a flow-through apparatus includes a rectangular channel, removable insert, and allows for view of both a compact sample as well as fluid flow through the channel. The apparatus can be fabricated from a block of Lexan plastic, machined and adapted to fit all of the aforementioned components. Lexan plastic is generally inexpensive and possesses good optical qualities. However, Lexan is not suitable for Raman microscopy, a method that can be used to detect changes of the compact sample during dissolution. Lexan plastic has been found to have its own Raman signal that could interfere with the sample's Raman signal. Accordingly, Lexan plastic should be modified to include pieces of glass to cover areas that might potentially be scanned with a Raman microscope, i.e., the top face of the drug and the channel. In an exemplary embodiment, the base of the apparatus is plastic and is adapted to allow the compact to be observed from most angles. FIG. 4 illustrates an exemplary flow-through apparatus 40 associated with the present disclosure made from plastic having a flow-through channel 41 and adapted to allow for insertion of an insert 10 into an opening 42.

Figure 5:
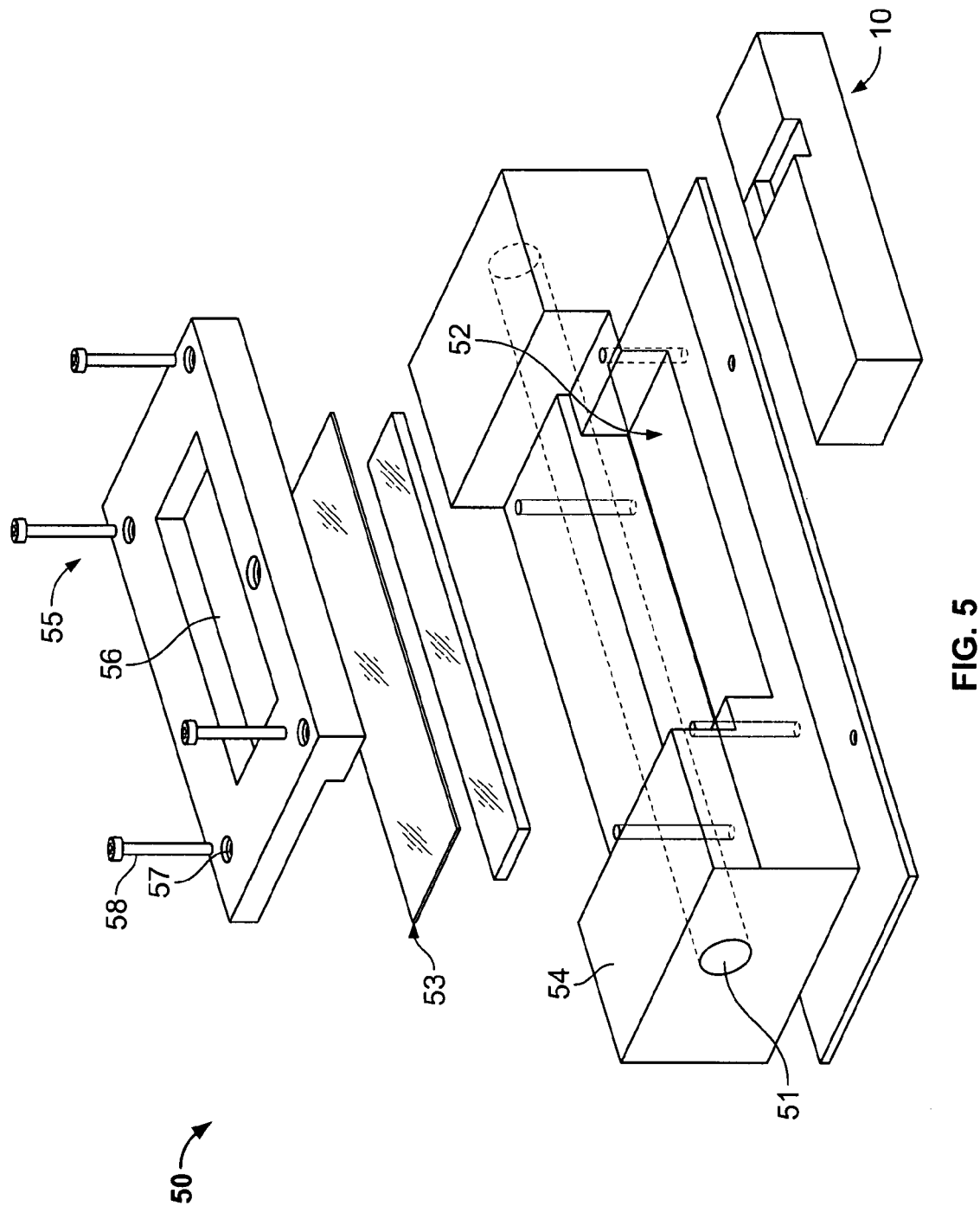
FIG. 5 illustrates an exploded view of an exemplary flow-through apparatus associated with the present disclosure.
Figure 6:
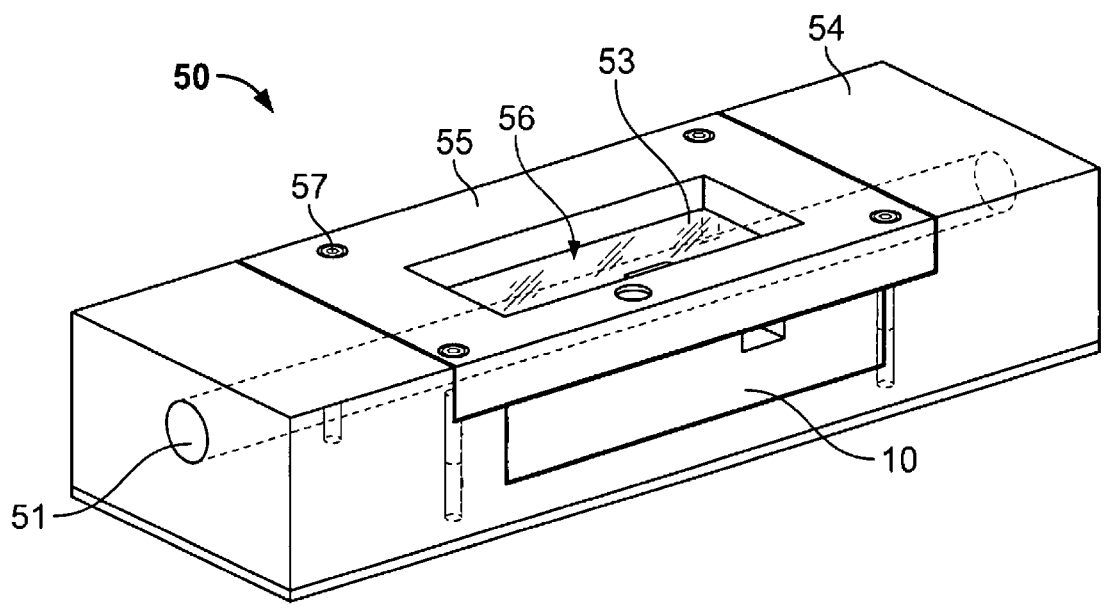
FIG. 6 illustrates an assembled exemplary flow-through device associated with the present disclosure of FIG. 5.

In an exemplary embodiment, a flow-through apparatus is modified to include glass plates as shown in FIG. 5 and FIG. 6. FIG. 5 illustrates an exploded view of an exemplary flow-through apparatus 50 having a flow-through channel 51 and glass plates 53. Apparatus 50 is adapted to receive insert 10 into an opening 52. In an exemplary embodiment, base dimensions of apparatus 50 are 75 mm×40 mm, which is approximately the size of a typical microscope slide. The height of apparatus 50 is about 1.5 cm. Once assembled, apparatus 50 creates a generally rectangularly shaped flow channel 51. A compact sample 14 is positioned such that it is observable through a front wall 54 of apparatus 50. Compact 14 is positioned away from the corners of channel 51. This positioning minimizes corner effects. Apparatus 50 is adapted to be placed on a microscope stage and to receive lighting from the top, permitting a user to look down onto compact sample 14 and channel 51. FIG. 6 illustrates an assembled view of apparatus 50.

Figure 7:
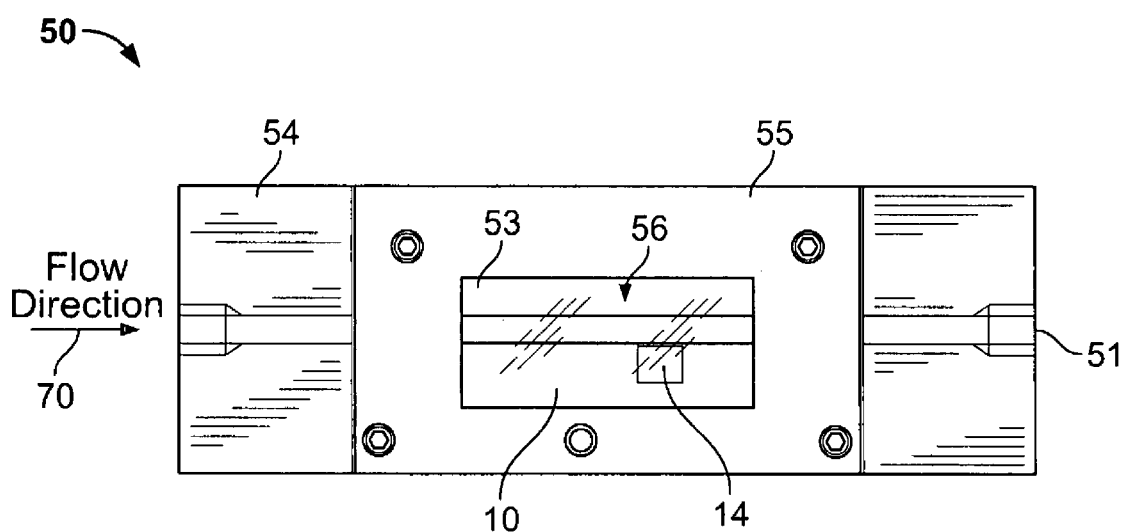
FIG. 7 is a top down view of an exemplary flow-through apparatus of FIG. 6.

Typically, glass plates 53 are secured in place on vertical wall 54 via a securing mechanism 55. Securing mechanism typically defines a rectangular opening 56 to allow viewing through glass plates 53 and four securing apertures 57 adapted to receive a bolting means 58 (e.g., a screw or bolt). FIG. 7 illustrates a front face view of an assembled apparatus 50. In an exemplary embodiment, a fluid flows through channel 51 in a flow direction 70 interacting with one planar face of compact sample 14. As shown in FIG. 7, dissolution and flow is visible through glass plate 53 on front wall 54. Front wall 54 is typically rectangular in shape with the elongated side parallel with flow direction 70. Thus, flow direction 70 can be in either direction, i.e., left-to-right or right-to-left.

Figure 8:
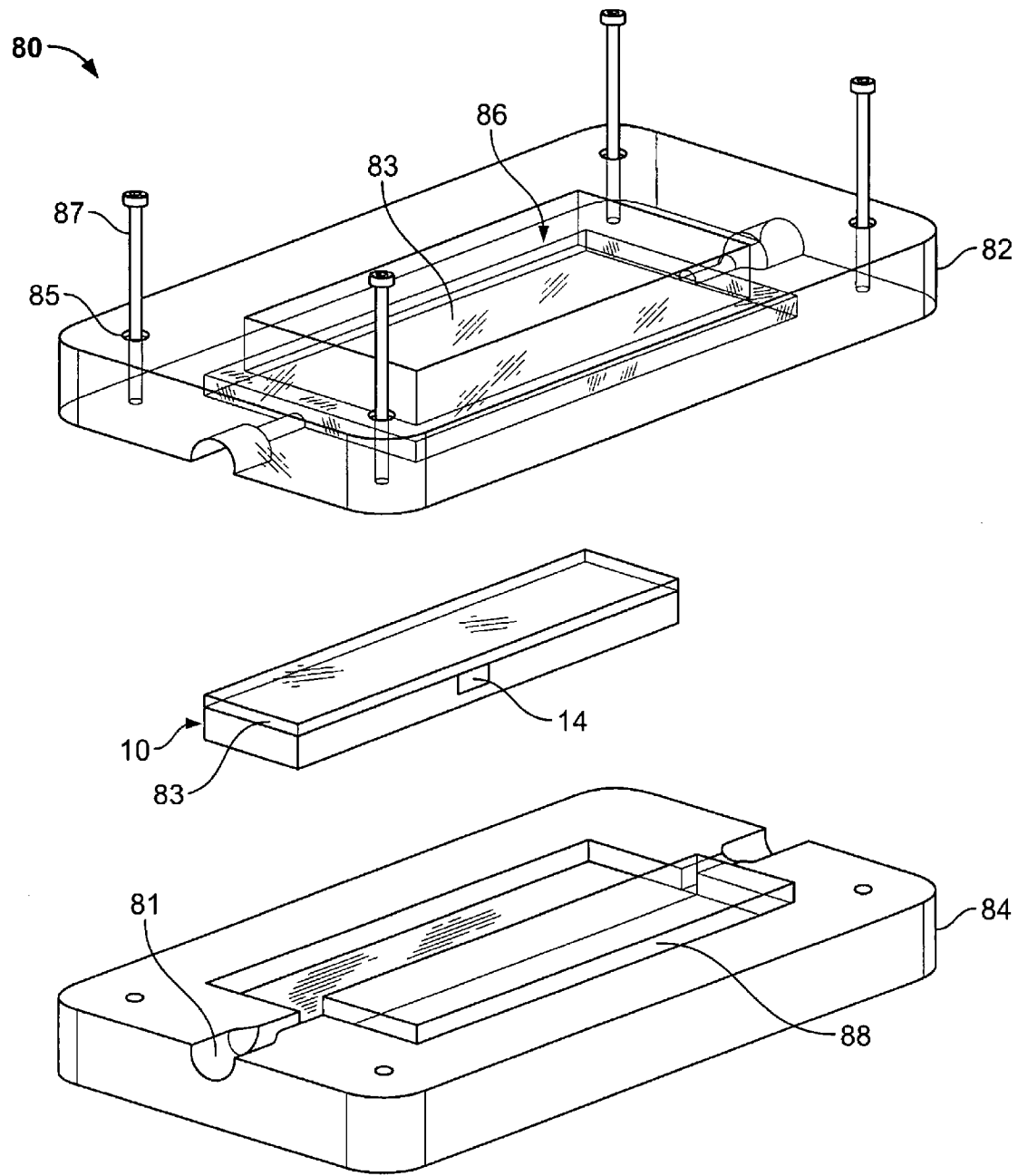
FIG. 8 is an exploded view of an exemplary flow-through apparatus associated with the present disclosure illustrating a glass plate embodiment.

FIG. 8 illustrates an exploded view of an exemplary embodiment of a flow-through apparatus 80 associated with the present disclosure. Apparatus 80 includes two thin plates of glass 83 surrounded in a stainless steel frame made up of a top portion 82 and a bottom portion 84. Positioned within top portion 82 and bottom portion 84 is a removable insert 10. Similar to apparatus 50 shown in FIG. 7, apparatus 80 defines an opening 86 to allow viewing of the dissolution of the compact sample 14. Once assembled, apparatus 80 defines a flow channel 81. Fluid passing through flow channel 81 and compact sample 14 interact in a similar manner as previously described in other embodiments. Top portion 82 and bottom portion 84 are both made of stainless steel and virtually identical in shape and size. Top portion 82 and bottom portion 84 each define four apertures 85 positioned in the corners and adapted to receive securing means 87. Securing means 87 can be any means of securing the apparatus, such as a screw or a bolt.

Figure 9:
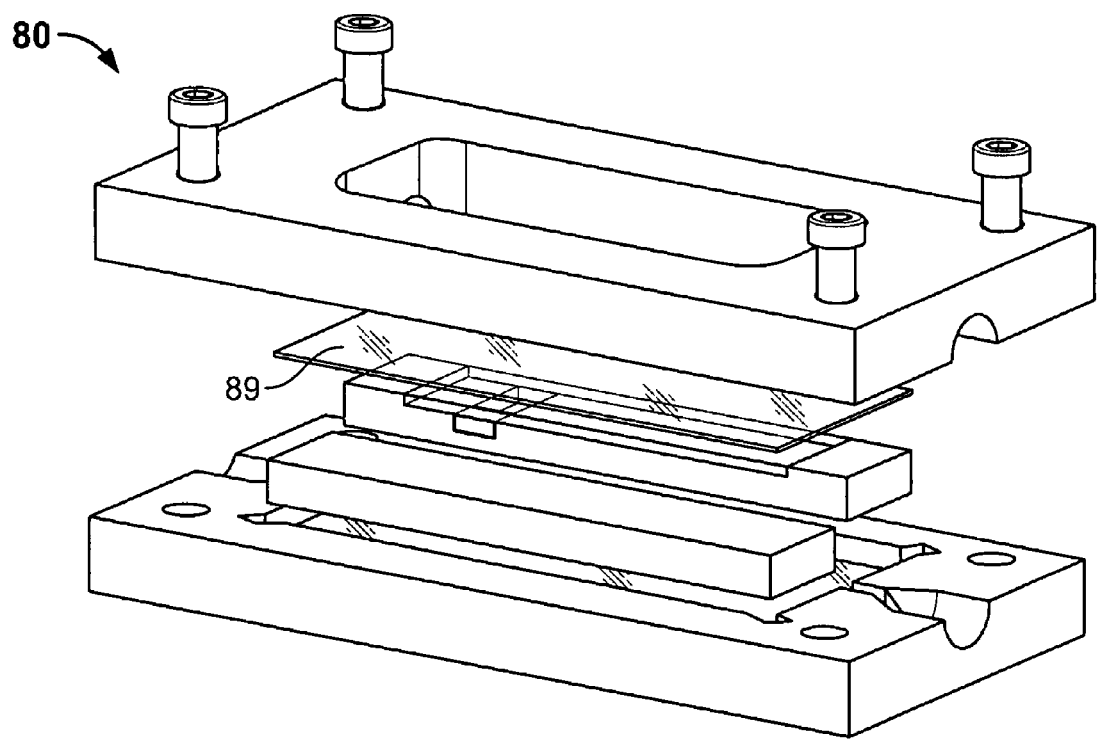
FIG. 9: is an exploded view of an exemplary flow-through apparatus associated with the present disclosure illustrating a multi-glass plate embodiment.
Figure 10:
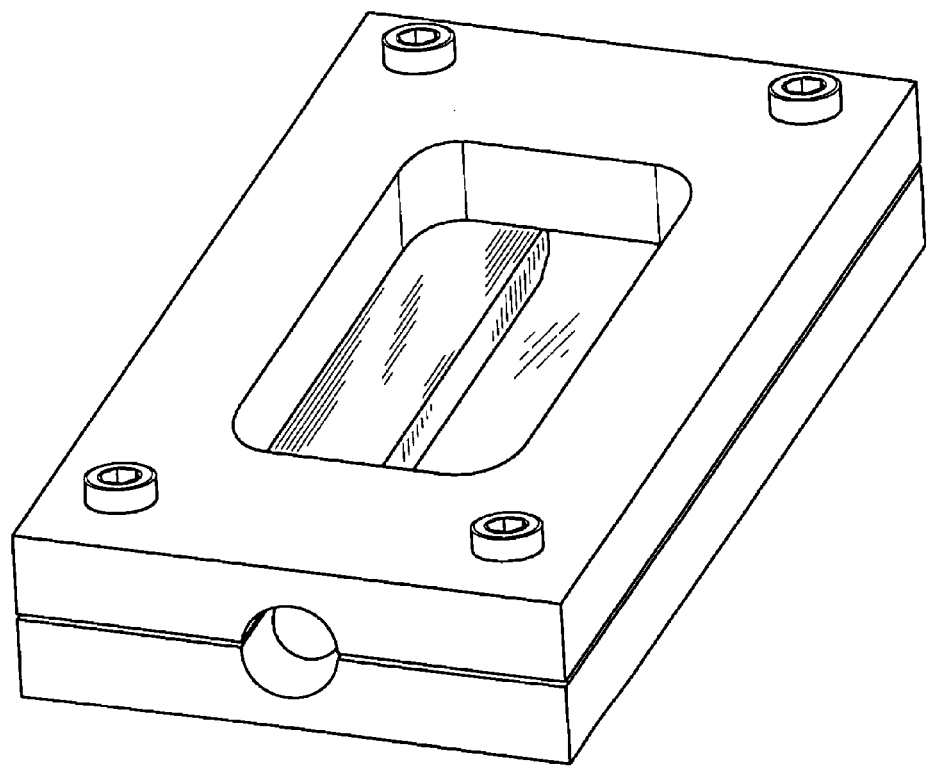
FIG. 10 illustrates an assembled view of the exemplary flow-through apparatus of FIG. 9.

In an exemplary embodiment, insert 10 is also stainless steel. Apparatus 80 includes a block 88 which can be made of plastic and be adapted to create a wall of flow channel 81 to guide fluid flow. Flow guide block 88 can be made from Lexan plastic which offers advantageous thermal-insulating properties over stainless steal. Glass plates 83 can be typical microscope coverslips. In an exemplary embodiment, a third plate of glass is positioned within opening 86 and is a microscope slide that is cut to an appropriate dimension. FIG. 9 illustrates an exploded view of an exemplary apparatus 80 having microscope coverslip 89. FIG. 10 illustrates an assembled embodiment of apparatus 80. In an exemplary embodiment, insert 10 and block 88 are made of aluminum.

Figure 11A:
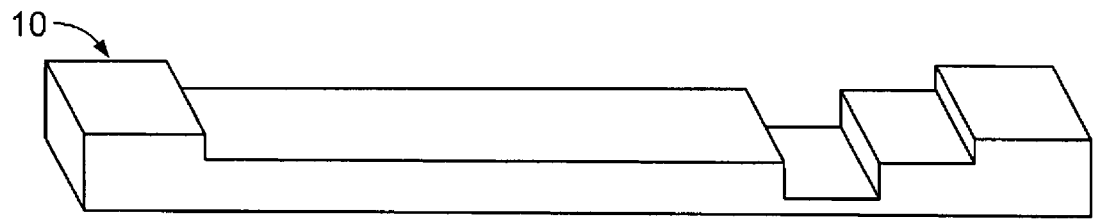
FIG. 11(a) illustrates an exemplary insert having a recessed cavity for a glass insert.
Figure 11B:
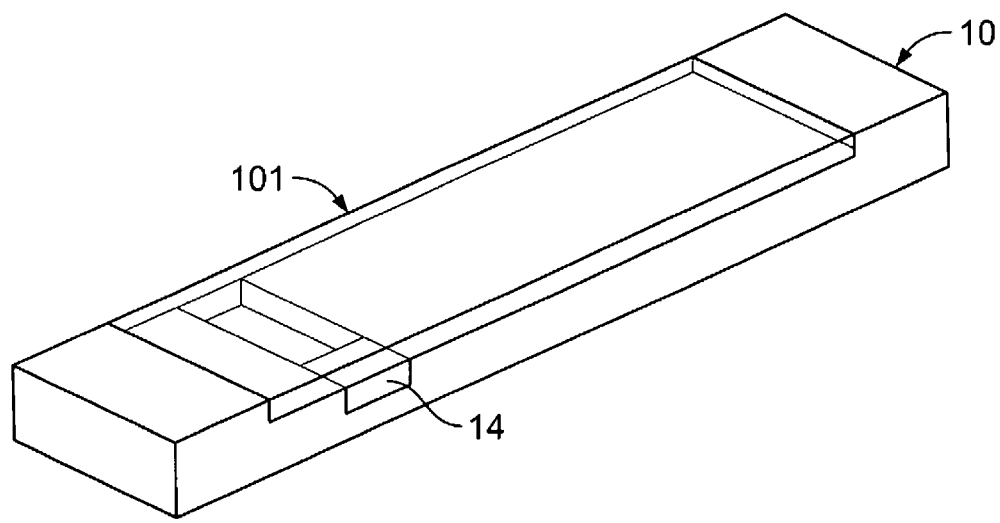
FIG. 11(b) illustrates an exemplary insert having a recessed cavity for a glass insert with a glass plate and a compact sample.

To ensure proper flow through functionality, an apparatus associated with the present disclosure should be water tight, i.e., when fluid passes through, there will be virtually no leaks. In an exemplary embodiment, a sealant is applied between each of the parts of the disclosed apparatus to ensure appropriately tight fits. Typical sealants should be temporary, non-hardening substances since the cell is designed to be taken apart and put together many times. Petroleum-based vacuum grease can be used as a sealant in an exemplary apparatus. In an exemplary apparatus, a thin rubber gasket layer is added between top and bottom portions of the apparatus to better control leaks. In particular embodiments, the glass components may be fragile and may crack if too much force is applied when tightening the securing means. In order to facilitate assembly in an exemplary embodiment, the insert is designed such that the glass covers are restricted. FIG. 11 illustrates an exemplary insert 10 wherein a glass cover 101 is restricted and assembled within insert 10 such that assembly into an apparatus 80 will be easier, thereby reducing the potential for breaking of the glass components.

Typically, fluid delivery is accomplished by a pumping mechanism such as a hydrostatic reservoir, peristaltic pump, and/or a syringe pump. A hydrostatic reservoir is typically less expensive than other mechanisms, however, flow control is more difficult. A peristaltic pump may introduce some undesired oscillatory effects to the flow through the channel. A syringe pump (i.e., Model #780230, KDScientific, Holliston, Mass.) uses up to four 140 mL syringes in parallel to deliver a fluid. A syringe pump typically has a high degree of precision relative to the rate of flow produced. In an exemplary embodiment, a syringe pump will have a range of flow rates from 0.01 mL/min to 140 mL/min. Drawbacks associated with the syringe pump arise when running a test for an extended period of time since the syringe pump needs to be refilled frequently. Although reference is made to exemplary pumps for fluid delivery, it is understood that the present disclosure is not limited to those described and alternative pumps are within the scope of the present disclosure.

An exemplary apparatus may use pre-manufactured glass coverslips which can typically be ordered from any chemistry supply catalogue. Glass coverslips should be adapted to fit appropriately within an apparatus such that the flow of a fluid and the dissolution can be observed by microscopy and satisfy desired precision parameters.

When in contact with oxygen, aluminum forms a protective aluminum oxide layer that helps it resist corrosion. This works well against water. However, if the flow-through fluid is an HCl solution, protons in the solution react with the aluminum oxide, stripping the aluminum of its protective layer. Typically after about an hour in HCl solution, aluminum becomes pitted and corroded. In addition to the corrosion, a gaseous reaction product is formed causing bubbles to form, which confounds dissolution results. Thus, in an exemplary embodiment, apparatus 80 is made almost entirely out of stainless steel.

An important element in designing an exemplary flow-through apparatus according to the present disclosure is flow channel geometry. The length of an apparatus is advantageously limited by the size of a microscope stage (approximately the length of a microscope slide). The height and width of a channel effect the hydrodynamic entry length and velocity distribution along a compact sample. Computational fluid dynamics (CFD) can be used to determine the velocity distribution near the samples surface. Additionally, in order to determine whether the velocity profile is fully developed at the compact position, hydrodynamic entry length can be obtained using theoretical calculations and using CFD. CFD software available in the market such as Fluent can be used to accomplish velocity profiling. The hydrodynamic entry length is important in the determination of what limits can be set for flow rates while assuring fully developed laminar flow past the compact. Also important is determining which geometry leads to the shortest entry length, as shorter entry lengths allow for a wider range of flow rates to be feasible.

EXAMPLE 1

Flow profiles through rectangular channels of 4×4 mm, 6×2 mm, and 4×2 mm were analyzed using CFD. Prior to using CFD, however, the proper geometries for exemplary channels were created using GAMBIT software (Fluent, Inc., Lebanon, N.H.). 3D rectangular volumes with various cross sectional geometries (4×4 mm, 4×2 mm, 6×2 mm) were created. Simple rectangular meshes were set up to consist of around 150,000 nodes, fine enough to accurately represent the velocity profiles. This mesh was of constant interval size, which led to convergence of the solution in CFD in less than 1 hour. Boundary types were also selected in GAMBIT. Inlets were set as velocity inlets, outlets were pressure outlets, and all walls were set as walls.

In CFD, various parameters were set up for each case. The boundary conditions set in GAMBIT were further described based on what kind of tests were to be performed. For the initial velocity tests, the energy equation was not solved. Material properties were taken from the CFD database. Water was used as the fluid and was given a density of 1 g/cm$^3$, and viscosity of 1 cP. The inlet velocity was adjusted for various trials. These velocities provide a wide enough spectrum of results to represent the full range of velocities that are expected in an actual experimental setup.

To examine the effects of various geometries on the velocity distribution near a compact sample, cross sectional views of an exemplary channel were taken at a distance of 40 mm away from the inlet. This was the original position proposed for a compact sample, assuming it is far enough from the inlet to allow for fully developed flow and a wide range of flow rates. Since no slip boundary conditions were applied, the velocity of the fluid at the exact location of the compact surface was zero, and therefore to analyze the variation of velocities in the region of the compact, values for velocity were taken at a distance of 0.2 mm away from the compact surface.

Figure 12:
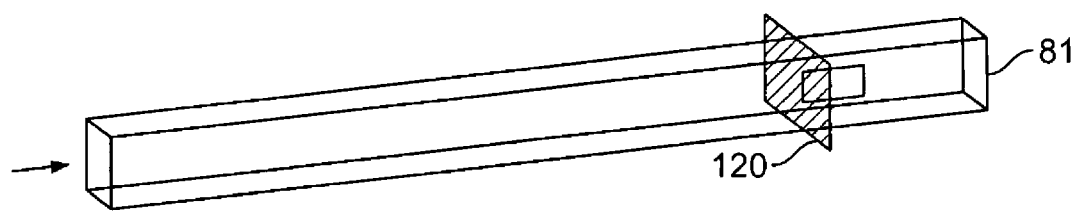
FIG. 12 illustrates a schematic of a cross section of an exemplary flow-through channel.
Figure 13:
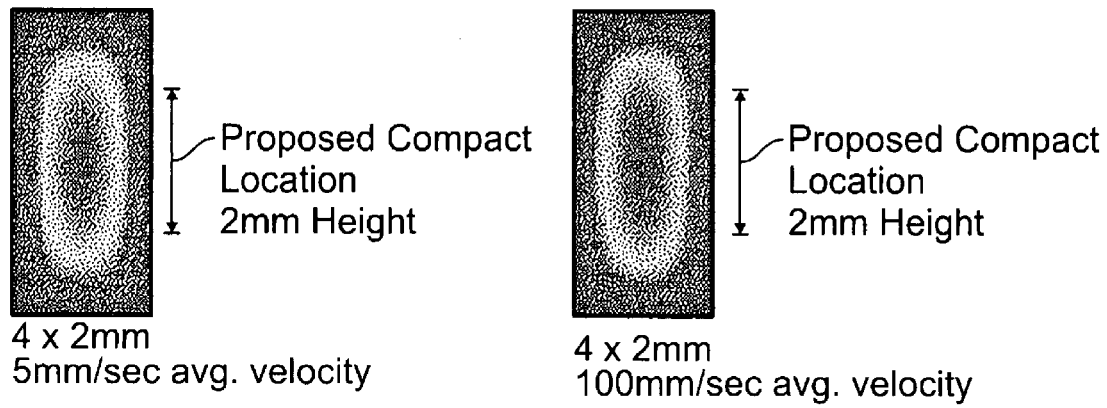
FIG. 13 is a cross section flow velocity profile in a 4×2 mm channel at 5 mm/sec and 100 mm/sec.
Figure 14:
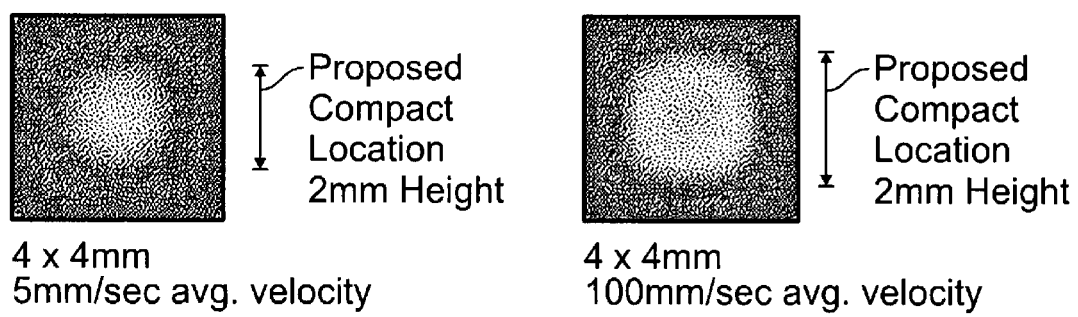
FIG. 14 is a cross section flow velocity profile in a 4×4 mm channel at 5 mm/sec and 100 mm/sec.
Figure 15:
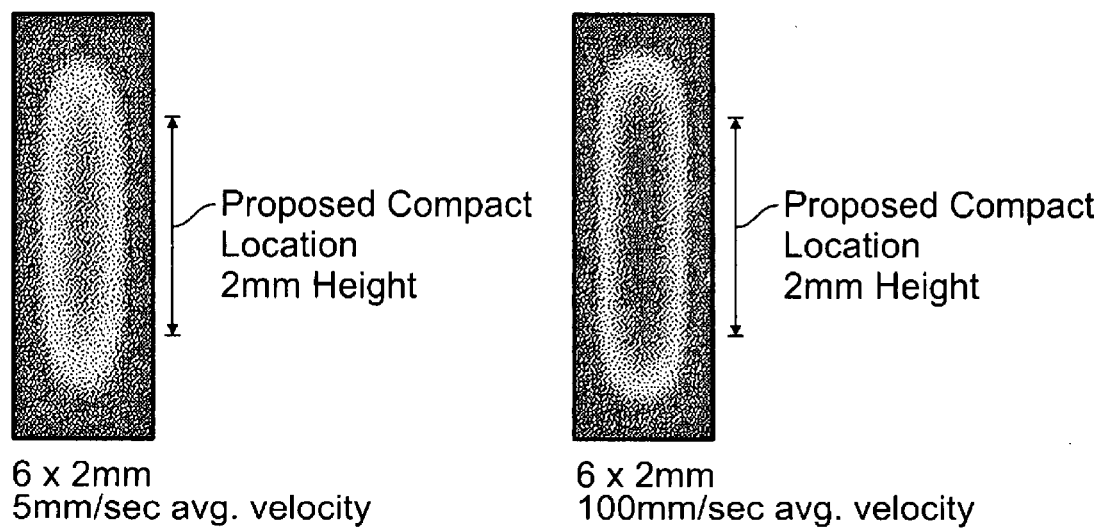
FIG. 15 is a cross section flow velocity profile in a 6×2 mm channel at 5 mm/sec and 100 mm/sec.

FIG. 12 illustrates a schematic of a cross section 120 in an exemplary channel 81. FIG. 13, FIG. 14, and FIG. 15 are cross sectional views of each of three exemplary geometries (4×2 mm, 4×4 mm, and 6×2 mm) for average flow velocities of 5 mm/sec and 100 mm/sec. Referring to FIG. 13, in the 4×2 mm channel, the variation of velocity over the compact surface is about 10% for both 5 mm/sec and 100 mm/sec average flow velocities. In the square channel, illustrated in FIG. 14, the velocity above the compact surface 0.20 mm into the fluid flow from the compact location has a significant amount of variation. In the 5 mm/sec section, the variation from the center of the compact to its upper or lower edge is as much as 25%. This variation is slightly less at an average flow velocity of 100 mm/sec.

Referring to FIG. 15, there is significantly less variation in velocity over the surface of the compact in a 6×2 mm channel. For both the 5 mm/sec average velocity and the 100 mm/sec average velocity flows, there is only a 5% variation of velocity over the compact surface. However, the 6×2 mm channel reduces the ability to analyze the dissolution medium adjacent to the compact because of the 2 mm depth from the coverslip to the dissolving boundary. Of course, in the 6×2 mm channel, a wider compact, e.g., 4×4 mm, could be used. The 6×2 mm channel with a 4×4 mm compact is not conducive to confocal microscopy because the increased thickness of the device would cause problems with focal length and requires double the amount of sample material. However, it could be useful in other types of microscopy wherein the total solution is analyzed for concentration of the dissolving solid.

Theoretical calculations were done to determine the hydrodynamic entry length for three channel sizes, 4×4 mm, 4×2 mm, and 6×2 mm. For the fluid flow to be considered fully developed, the shape of the velocity vectors representing the fluid flow must be parabolic in shape. The hydrodynamic entry length equation is:

$$x_{fd,h} = 0.05 Re * D_h \quad \text{(Equation 1)}$$

Where:

$$Re = \frac{\rho v D_h}{\mu} \quad \text{(Equation 2)}$$

$$D_h = \frac{4A}{P} \quad \text{(Equation 3)}$$

Figure 16:
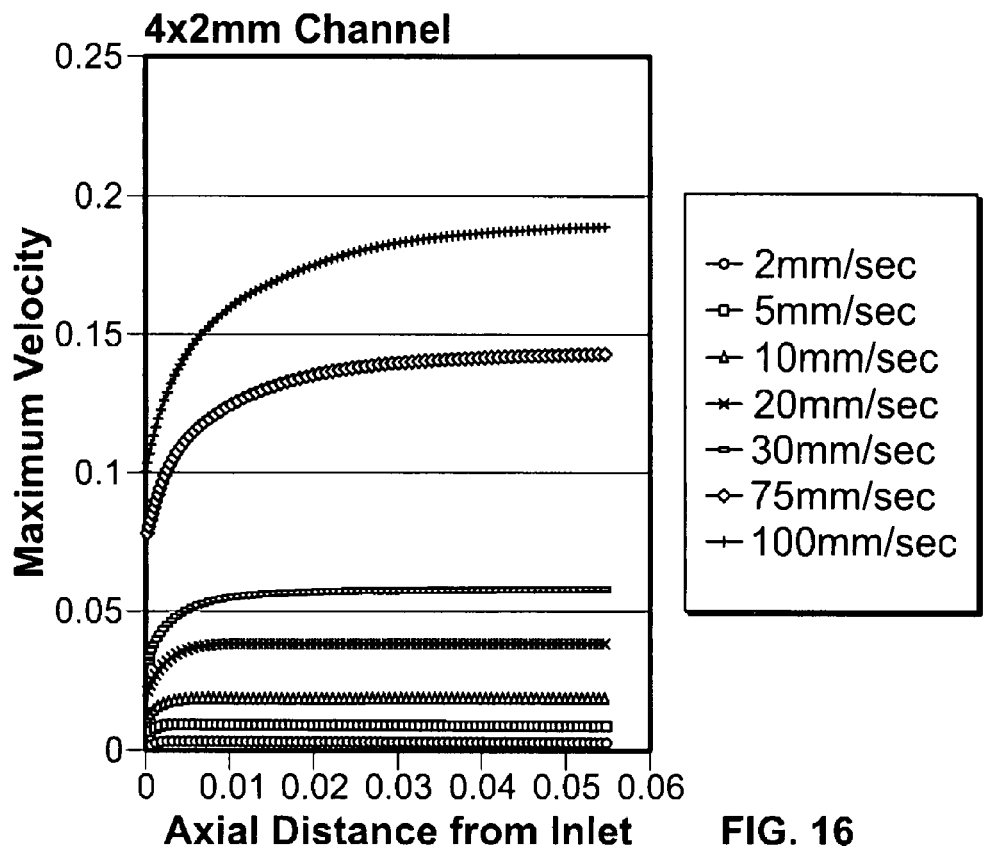
FIG. 16 is a graph of evolution of velocity profile in a 4×2 mm channel.
Figure 17:
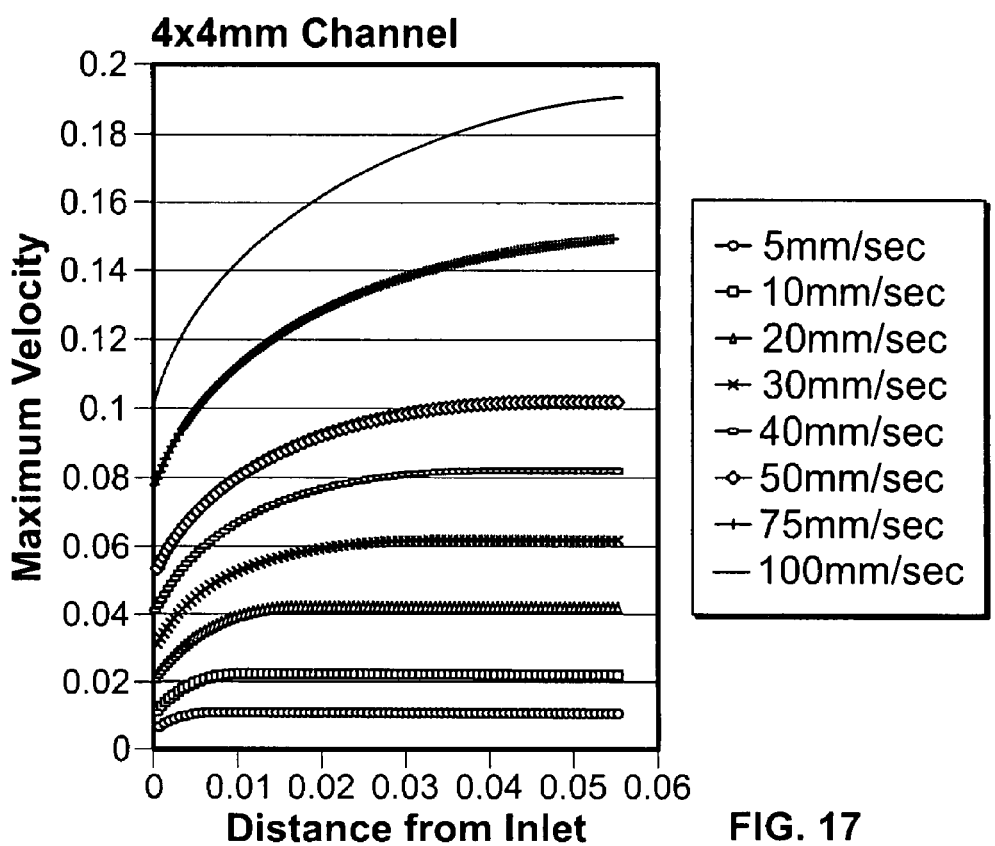
FIG. 17 is a graph of evolution of velocity profile in a 4×4 mm channel.
Figure 18:
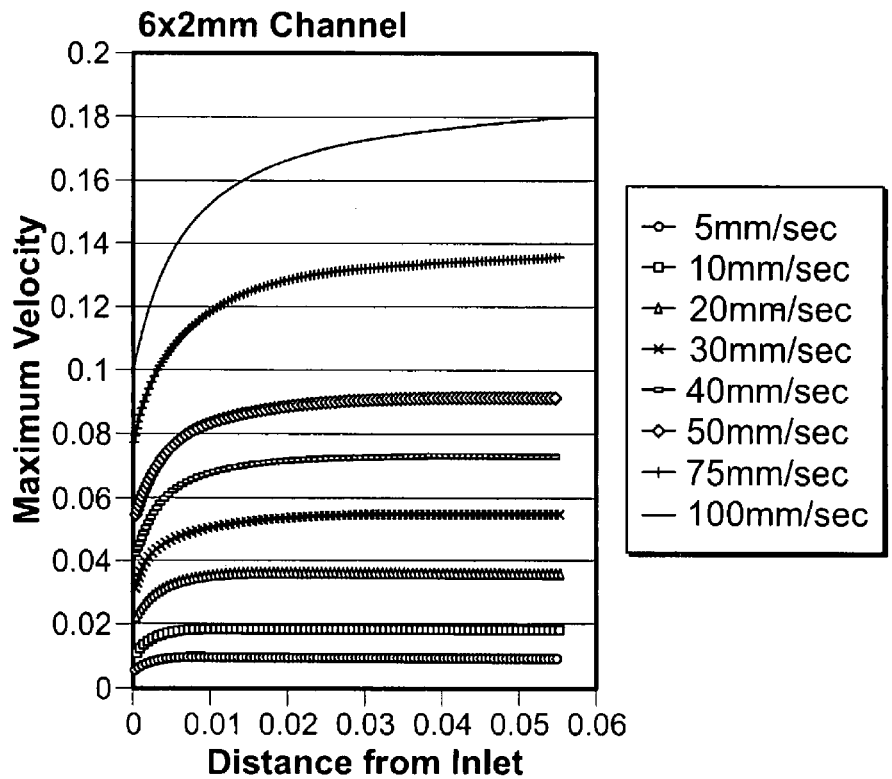
FIG. 18 is a graph of evolution of velocity profile in a 6×2 mm channel.

$x_{fd,h}$ = hydrodynamic entry length $Re$ = Reynolds number $\rho$ = density $v$ = velocity $D_h$ = hydraulic diameter $\mu$ = viscosity $A$ = cross sectional area $P$ = wetted perimeter Hydrodynamic entry lengths for various geometries and flow velocities were examined using CFD. To predict the hydrodynamic entry lengths in CFD, a line was drawn down the center of the channel. When the flow is fully developed, the maximum reported fluid velocity is constant along the centerline, i.e., the slope of the plotted velocity vs. distance curve was 0. The location at which the value of the slope between two points varied 1% or less is the location at which the flow was determined to be fully developed. The lead edge of the compact was proposed to be located 40 mm down the channel from the inlet, so it is critical that the curve of the maximum velocity at this location have a slope of zero. The velocity profile developed most rapidly in the 4×2 mm channel as compared to the other channel geometries as shown in FIG. 16 (4×2 profile), FIG. 17 (4×4 profile), and FIG. 18 (6×2 profile). These results can be compared to the theoretical calculated hydrodynamic entry lengths as shown in Table 1 below.

TABLE 1

Comparison of Channel Sizes - Hydrodynamic Entry Length

| Geometry | Avg. Flow Velocity (mm/s) | Entry Length in mm (CFD) | Entry Length in mm (theoretical calculation) |
|---|---|---|---|
| 4 × 2 mm | 5 | 2.9 | 1.8 |
| | 10 | 6.3 | 3.6 |
| | 20 | 11 | 7.1 |
| | 30 | 16 | 10 |
| | 40 | 22 | 14 |
| | 50 | 31 | 18 |
| | 100 | >50 | 35 |
| 4 × 4 mm | 5 | 7.6 | 4.0 |
| | 10 | 14 | 8.0 |
| | 20 | 27 | 16 |
| | 30 | 41 | 24 |
| | 50 | >50 | 40 |
| | 100 | >50 | 80 |
| 6 × 2 mm | 5 | 4.8 | 2.3 |
| | 10 | 9.0 | 5.5 |
| | 20 | 20 | 10 |
| | 30 | 32 | 17 |
| | 40 | 42 | 22 |
| | 50 | >50 | 28 |
| | 100 | >50 | 55 |

The CFD results differ significantly from the results of the hand calculations for hydrodynamic entry length. For these analyses, the results given by CFD are considered more accurate, as no simplifying assumptions are made in the simulation, unlike the theoretical calculations for which the rectangular channel is simplified into a round pipe via the hydraulic diameter conversion. General trends are the same, however, in both the CFD simulations and the theoretical calculations. The flow in the 4×4 mm channel takes the most distance to develop, and the flow in the 4×2 mm channel develops most rapidly. Therefore, of the three channel geometries described, the 4×2 mm channel will allow flow to develop most rapidly, and a wider range of flow rates can be used in the channel.

After analyzing three velocity simulations it was determined that an effective channel geometry is 4×2 mm. The length was set at 50 mm, due to limitations on the overall size of the flow-through apparatus. The hydrodynamic entry length in a 4×2 mm channel is shorter than that of either of the two other possible configurations (see, e.g., Table 1). Since the hydrodynamic entry length is shorter for the 4×2 mm channel, a larger range of flow rates are possible as compared to the alternative channel sizes. The other main advantage to the 4×2 mm geometry is that it has the smallest cross section, which will lead to the smallest volumetric flow rate required to obtain a desired linear flow velocity through a channel. This, in turn, will allow for experiments to run for a longer period of time for a fixed volume of dissolution medium.

A 4×2 mm configuration is found to be ideal for both velocity distribution and viewing requirements. The taller a channel becomes, e.g., a 6×2 mm design, the larger the gap becomes between the top edge of the glass and a 2×4 mm compact sample. However, a channel with smaller dimensions (less than 4×2 mm) may become difficult to machine, and while it may further reduce the gap between the upper compact edge and the top of the channel, fabrication costs may rise. It is noted that the CFD simulations show that the dimensions of the flow cell could be shortened at lower flow rates. However, microscope slide dimensions may have appeal in certain applications.

EXAMPLE 2

Shear stresses and rates over a compact surface were modeled using CFD for comparison to existing dissolution apparatus and in vivo. In an existing dissolution device, a USP II apparatus, shear stresses and shear rates have been modeled using CFD. (See, e.g., Kukura, J., J. L. Baxter, and F. J. Muzzio, Shear distribution and variability in the USP Apparatus 2 under turbulent conditions, International Journal of Pharmaceutics, 2004, 279(1-2): p. 9-17.) In addition to these reported results, a paper by Abrahamsson models the shear stresses experienced by a compact in the human fed stomach by CFD. (See, e.g., Abrahamsson, B., et al., A Novel in Vitro and Numerical Analysis of Shear-Induced Drug Release from Extended-Release Tablets in the Fed Stomach, Pharmaceutical Research, 2005, 22(8): p. 1215-1226.) These results were taken into consideration as a comparison for the shear stresses experienced in a flow-through apparatus associated with the present disclosure.

Abrahamsson reported shear stresses that are in the range of 1-7 Pa on average, with fluctuations up to 50 Pa. For a USP II apparatus, reported shear stresses fall in the range of 0.01 to 0.02 Pa. In an apparatus associated with the present disclosure, shear stresses were examined for flow rates between 1 and 70 mL/min. A simulation was run assuming steady state conditions in a channel. Shear stresses between 0.002 and 0.4 Pa were reported for this range of flow rates, which compared closely to the reported values seen in the USP II. However, shear stresses nearly 20 times larger were reported in the human stomach. This is due to the viscosity of the stomach fluid modeled by Abrahamsson being far greater than the viscosity of water, which is the fluid used in both the flow cell and USP II. Therefore, to normalize the results, shear rates were examined, which are calculated by the following formula:

$$\gamma = \frac{\tau_{shear}}{\mu} \qquad \text{(Equation 4)}$$

Where:

$\gamma$ = shear rate (s$^{-1}$)

$\tau$ = shear stress (Pa)

$\mu$ = viscosity (Ns/m$^2$)

This allowed for a proper comparison of shear, with results reported in Table 2:

TABLE 2

Shear comparison between various dissolution apparatuses and simulations.

| Device | Shear Stress (Pa) | Viscosity (N s/m$^2$) | Shear Rate (s$^{-1}$) |
|---|---|---|---|
| USP II | 0.01-0.02 | 0.001 | 10-20 |
| Abrahamsson Model | 1-7 | 0.01-2.0 | 100-700 (low viscosity) to 0.5 to 3.5 (high viscosity Average 5-35 |
| Flow Cell | 0.002-0.4 | 0.001 | 2-400 |

The ranges of shear rates vary significantly; however, when the extreme values of shear rate for each case are ignored, the Abrahamsson model predicts shear rates in the range of 5-35 s$^{-1}$, and the flow-through apparatus produces shear rates from 5-60 s$^{-1}$. Data analyses show that the shear rates in the apparatus associated with the present disclosure, USP II and human fed stomach are similar, confirming that the flow-through apparatus will be capable of producing dissolution rates of value relative to those in USP II apparatus, as well as the human stomach.

EXAMPLE 3

It is desirable to compare fluid flow in an exemplary apparatus associated with the present disclosure with that in the rotating disk apparatus to correlate existing data. The rotating disk or Wood's Die apparatus was chosen as a comparator because the hydrodynamics and mass transport are well known and characterized. (See, e.g., Levich, V. G., Physicochemical Hydrodynamics. 1962. 700 pp.) To establish a relationship between rotating disk speed and volumetric flow rate for an exemplary channel of a flow-through apparatus, fluxes are equated in each apparatus.

Flux of a drug from a rotating disk is described as:

$$J = 0.62 D^{2/3} \nu^{-1/6} \omega^{1/2} C_s \qquad \text{(Equation 5)}$$

The dissolution rate for a drug compact in a rectangular channel is:

$$R = 1.468 Q^{1/3} D^{2/3} C_s b \left(\frac{L^2}{H^2 W}\right)^{1/3} \qquad \text{(Equation 6)}$$

To convert this into a flux, divide by area.

$$J = 1.468 A^{-1} Q^{1/3} D^{2/3} C_s b \left(\frac{L^2}{H^2 W}\right)^{1/3} \qquad \text{(Equation 7)}$$

When we equate the flux in Equation 5 and Equation 7, solve for $\omega^{1/2}$ and substitute the flow cell tablet area for A, ($6.8*10^{-6}$ m$^2$) we obtain the relationship.

$$\omega^{1/2} = 2.37 A^{-1} b \nu^{-1/6} \left(\frac{L^2}{H^2 W}\right)^{1/3} Q^{1/3} \qquad \text{(Equation 8)}$$

Where:

$J$ = flux (g/m$^2$ * s)

$R$ = Dissolution rate (g/s)

$\omega$ = rotation speed (1/s)

$D$ = Diffusion Coefficient (m$^2$/s)

$C_s$ = Solubility (g/m$^3$)

$b$ = height of tablet in flow cell (0.0017 m)

$\nu$ = kinematic viscosity of water (10$^{-6}$ m$^2$/s)

$Q$ = volumetric flow rate (m$^3$/s)

$L$ = length of tablet in flow cell (0.004 m)

$W$ = width of channel (0.002 m)

$H$ = height of channel (0.004 m)

This analysis yields a relationship between Q and ω which will give an equal value of flux. (Note that the area of the drug compact is smaller than specified in theory. The discrepancy in size is due to the fabrication process, the area shown here is the actual area in the flow cell used.)

The results are shown in Table 3:

TABLE 3

Relationship between Rotation Speed in Rotating Disk Apparatus and Volumetric Flow Rate in Flow cell to obtain same dissolution rate of nonreactive solids

| | Volumetric Flow Rate (ml/min) | | | | | | | | |
|---|---|---|---|---|---|---|---|---|---|
| | 1.0 | 2.5 | 5.0 | 7.5 | 10.0 | 12.5 | 15.0 | 17.5 | 20.0 |
| Rotation Speed (rpm) | 3 | 40 | 64 | 84 | 101 | 118 | 133 | 147 | 161 |

EXAMPLE 4

Shear stress is an important factor in the dissolution of solid drug samples, particularly those that convert at or near the surface. Here, an expression was derived for the shear stress in a rotating disk. Also, shear stress in an exemplary flow-through apparatus has been calculated using CFD. The derivation for shear stress in a rotating disk apparatus is described below.

Shear stresses in cylindrical coordinates are defined as:

$$\tau_{r\varphi} = -\mu \left[ r \frac{\partial}{\partial r}\left(\frac{v_\varphi}{r}\right) + \frac{1}{r} \frac{\partial v_\varphi}{\partial \varphi} \right] \quad \text{(Equation 9)}$$

$$\tau_{y\varphi} = -\mu \left[ \frac{1}{r} \frac{\partial v_y}{\partial \varphi} + \frac{v_\varphi}{\partial y} \right] \quad \text{(Equation 10)}$$

$$\tau_{yr} = -\mu \left[ \frac{\partial v_r}{\partial y} + \frac{\partial v_y}{\partial r} \right] \quad \text{(Equation 11)}$$

For rotating disk the velocity for each direction is described by:

$$v_r = 0.51023 r \sqrt{\frac{\omega^3}{\nu}}\, y \quad \text{(Equation 12)}$$

$$v_\varphi = r\omega - 0.616 r \sqrt{\frac{\omega^3}{\nu}}\, y \quad \text{(Equation 13)}$$

$$v_y = -0.51 \sqrt{\frac{\omega^3}{\nu}}\, y^2 \quad \text{(Equation 14)}$$

After substituting all necessary derivatives of the velocity components (Equations 12-14) into the shear stresses in cylindrical coordinates (Equations 9-11), two relevant shear stresses, tangential and radial are found:

$$\tau_{y\varphi} = -\mu \left[ -0.62 r \sqrt{\frac{\omega^3}{\nu}} \right] \quad \text{(Equation 15)}$$

$$\tau_{yr} = -\mu \left[ 0.51 r \sqrt{\frac{\omega^3}{\nu}} \right] \quad \text{(Equation 16)}$$

From these equations it is desired to find the total shear stress on a drug surface. Stress is a tensor which has nine components, the shear stresses and normal stresses. The only remaining components of the stress tensor are shown above. To find the resultant stress, the magnitude of the tensor must be determined. The magnitude of a tensor is given as:

$$|\underline{\tau}| = \sqrt{\frac{1}{2} \sum_{i,j} \tau_{i,j}^2} \quad \text{(Equation 17)}$$

Combining Equations 15-17 we find that the shear stress on the disk surface at y=0 is:

$$\tau = -\mu \left[ 0.80 r \sqrt{\frac{\omega^3}{\nu}} \right] \quad \text{(Equation 18)}$$

Equation 18 describes the shear stress at one value r. To find the average stress along the surface of the entire compact Equation 18 is integrated over radius, r.

$$\langle \tau \rangle = \frac{1}{r} \int_0^r -\mu \left[ 0.8 r \sqrt{\frac{\omega^3}{\nu}} \right] dr \quad \text{(Equation 19)}$$

Resulting in:

$$\langle \tau \rangle = -\mu \left[ 0.4 r \sqrt{\frac{\omega^3}{\nu}} \right] \quad \text{(Equation 20)}$$

Figure 19:
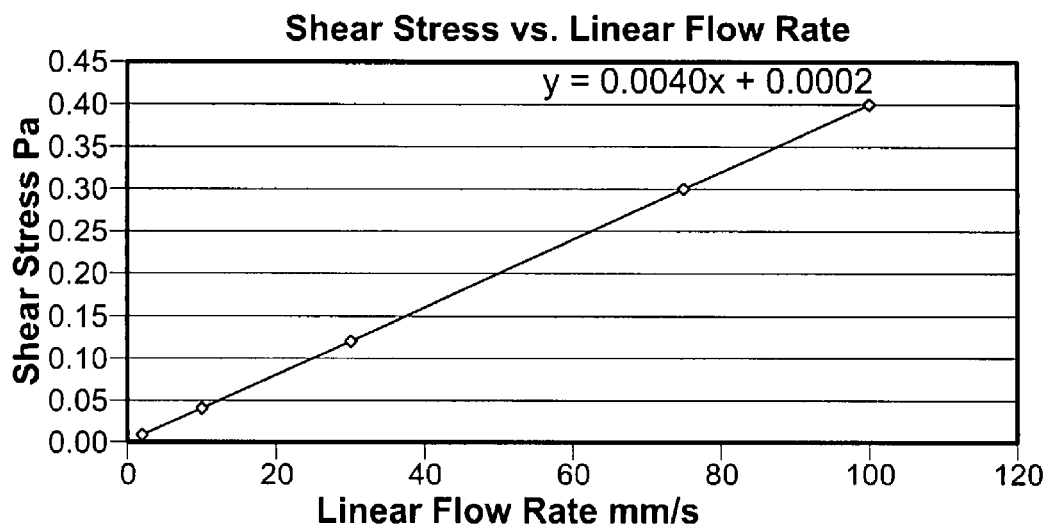
FIG. 19 is a graph of Shear Rate vs. Volumetric Flow Rate in a flow-through apparatus associated with the present disclosure.

Shear stress for flow through a 4×2 mm rectangular channel is found using CFD. The shear stress was calculated for five flow rates. It is expected that the shear stress is linearly related to the volumetric and linear flow rates. This is helpful since the shear rate and shear stress at any flow rate in the flow cell (for laminar flow) can be found. The results are shown in FIG. 19.

Table 4 shows the shear stresses at a compact surface for an exemplary flow-through apparatus (labeled 'flow cell') and rotating disk at several flow rates and rotation speeds. This table compares shear stresses for each apparatus at several flow rates/rotation speeds. The shear stress may be important for looking at salt precipitation once conversion has occurred.

TABLE 4

Shear Rate and Reynolds Number in Rotating Disk and Flow Cell Apparatus

| Flow Cell | | | Rotating Disk | | |
|---|---|---|---|---|---|
| mm/s | ml/min | Shear Stress (Pa) | rpm | rad/s | Shear Stress (Pa) |
| 1 | 0.41 | 0.004 | 10 | 1.0 | 0.002 |
| 2 | 0.82 | 0.008 | 15 | 1.6 | 0.003 |
| 3 | 1.22 | 0.012 | 20 | 2.1 | 0.005 |
| 4 | 1.63 | 0.010 | 25 | 2.6 | 0.007 |
| 5 | 2.04 | 0.020 | 30 | 3.1 | 0.009 |
| 6 | 2.45 | 0.024 | 35 | 3.7 | 0.011 |
| 7 | 2.86 | 0.028 | 40 | 4.2 | 0.014 |
| 8 | 3.26 | 0.032 | 45 | 4.7 | 0.016 |
| 9 | 3.67 | 0.036 | 50 | 5.2 | 0.019 |
| 10 | 4.08 | 0.040 | 55 | 5.8 | 0.022 |

TABLE 4-continued

Shear Rate and Reynolds Number in Rotating Disk and Flow Cell Apparatus

| Flow Cell | | | Rotating Disk | | |
|---|---|---|---|---|---|
| mm/s | ml/min | Shear Stress (Pa) | rpm | rad/s | Shear Stress (Pa) |
| 11 | 4.49 | 0.044 | 60 | 6.3 | 0.025 |
| 12 | 4.90 | 0.048 | 65 | 6.8 | 0.028 |
| 13 | 5.30 | 0.052 | 70 | 7.3 | 0.032 |
| 14 | 5.71 | 0.056 | 75 | 7.9 | 0.035 |
| 15 | 6.12 | 0.060 | 80 | 8.4 | 0.039 |
| 16 | 6.53 | 0.064 | 85 | 8.9 | 0.042 |
| 17 | 6.94 | 0.068 | 90 | 9.4 | 0.046 |
| 18 | 7.34 | 0.072 | 95 | 9.9 | 0.050 |
| 19 | 7.75 | 0.076 | 100 | 10.5 | 0.054 |
| 20 | 8.16 | 0.080 | 105 | 11.0 | 0.058 |
| 21 | 8.57 | 0.084 | 110 | 11.5 | 0.063 |
| 22 | 8.98 | 0.088 | 115 | 12.0 | 0.067 |
| 23 | 9.38 | 0.092 | 120 | 12.6 | 0.071 |
| 24 | 9.79 | 0.096 | 125 | 13.1 | 0.076 |
| 25 | 10.20 | 0.100 | 130 | 13.6 | 0.080 |
| 26 | 10.61 | 0.104 | 135 | 14.1 | 0.085 |
| 27 | 11.02 | 0.108 | 140 | 14.7 | 0.090 |
| 28 | 11.42 | 0.112 | 145 | 15.2 | 0.095 |
| 29 | 11.83 | 0.116 | 150 | 15.7 | 0.100 |
| 30 | 12.24 | 0.120 | 155 | 16.2 | 0.105 |
| 31 | 12.65 | 0.124 | 160 | 16.8 | 0.110 |
| 32 | 13.06 | 0.128 | 165 | 17.3 | 0.115 |
| 33 | 13.46 | 0.132 | 170 | 17.8 | 0.120 |
| 34 | 13.87 | 0.136 | 175 | 18.3 | 0.126 |
| 35 | 14.28 | 0.140 | 180 | 18.8 | 0.131 |
| 36 | 14.69 | 0.144 | 185 | 19.4 | 0.136 |
| 37 | 15.10 | 0.148 | 190 | 19.9 | 0.142 |
| 38 | 15.50 | 0.152 | 195 | 20.4 | 0.148 |
| 39 | 15.91 | 0.156 | 200 | 20.9 | 0.153 |
| 40 | 16.32 | 0.160 | | | |
| 41 | 16.73 | 0.164 | | | |
| 42 | 17.14 | 0.168 | | | |
| 43 | 17.54 | 0.172 | | | |
| 44 | 17.95 | 0.176 | | | |
| 45 | 18.36 | 0.180 | | | |
| 46 | 18.77 | 0.184 | | | |
| 47 | 19.18 | 0.188 | | | |
| 48 | 19.58 | 0.192 | | | |
| 49 | 19.99 | 0.196 | | | |
| 50 | 20.40 | 0.200 | | | |

EXAMPLE 5

Reynolds numbers for an apparatus associated with the present disclosure and a rotating disk apparatus have been calculated. Reynolds number for the flow cell was calculated using the hydraulic diameter (Equation 3). The Reynolds numbers (Re) of these apparatus should be compared with caution. The Re number describes the ratio of inertial forces to viscous forces of flow. Re helps distinguish laminar from turbulent flow. Laminar flow is a steady predictable flow, while turbulent flow is chaotic, time dependent and difficult to predict. It is important to note that there is not one Reynolds number for every geometry or physical situation that describes the transition from the laminar to turbulent regime. The critical Re (where flow become turbulent) is highly dependent on the physical situation and geometry of a system being studied. In the case of these apparatus, the critical Re for the flow cell is 2000, while the rotating disk critical Re is 10000-100000. Therefore in looking at Table 5 below, it is reasonable to conclude that flow rates associated with either apparatus are within the laminar flow region. It would not be reasonable to assume that at similar Re, these apparatus will exhibit similar dissolution profiles for the same drug.

TABLE 5

Reynolds numbers for Flow Cell and Rotating Disk

| Flow Cell | | | Rotating Disk | |
|---|---|---|---|---|
| mm/s | ml/min | Re | rpm | Re |
| 1 | 0.41 | 2.7 | 10 | 2.67 |
| 2 | 0.82 | 5.3 | 15 | 4.00 |
| 3 | 1.22 | 8.0 | 20 | 5.33 |
| 4 | 1.63 | 10.7 | 25 | 6.67 |
| 5 | 2.04 | 13.3 | 30 | 8.00 |
| 6 | 2.45 | 16.0 | 35 | 9.33 |
| 7 | 2.86 | 18.7 | 40 | 10.67 |
| 8 | 3.26 | 21.3 | 45 | 12.00 |
| 9 | 3.67 | 24.0 | 50 | 13.33 |
| 10 | 4.08 | 26.7 | 55 | 14.67 |
| 11 | 4.49 | 29.3 | 60 | 16.00 |
| 12 | 4.90 | 32.0 | 65 | 17.33 |
| 13 | 5.30 | 34.7 | 70 | 18.67 |
| 14 | 5.71 | 37.3 | 75 | 20.00 |
| 15 | 6.12 | 40.0 | 80 | 21.33 |
| 16 | 6.53 | 42.7 | 85 | 22.67 |
| 17 | 6.94 | 45.3 | 90 | 24.00 |
| 18 | 7.34 | 48.0 | 95 | 25.33 |
| 19 | 7.75 | 50.7 | 100 | 26.67 |
| 20 | 8.16 | 53.3 | 105 | 28.00 |
| 21 | 8.57 | 56.0 | 110 | 29.33 |
| 22 | 8.98 | 58.7 | 115 | 30.67 |
| 23 | 9.38 | 61.3 | 120 | 32.00 |
| 24 | 9.79 | 64.0 | 125 | 33.33 |
| 25 | 10.20 | 66.7 | 130 | 34.67 |
| 26 | 10.61 | 69.3 | 135 | 36.00 |
| 27 | 11.02 | 72.0 | 140 | 37.33 |
| 28 | 11.42 | 74.6 | 145 | 38.67 |
| 29 | 11.83 | 77.3 | 150 | 40.00 |
| 30 | 12.24 | 80.0 | 155 | 41.33 |
| 31 | 12.65 | 82.6 | 160 | 42.67 |
| 32 | 13.06 | 85.3 | 165 | 44.00 |
| 33 | 13.46 | 88.0 | 170 | 45.33 |
| 34 | 13.87 | 90.6 | 175 | 46.67 |
| 35 | 14.28 | 93.3 | 180 | 48.00 |
| 36 | 14.69 | 96.0 | 185 | 49.33 |
| 37 | 15.10 | 98.6 | 190 | 50.67 |
| 38 | 15.50 | 101.3 | 195 | 52.00 |
| 39 | 15.91 | 104.0 | 200 | 53.33 |
| 40 | 16.32 | 106.6 | | |
| 41 | 16.73 | 109.3 | | |
| 42 | 17.14 | 112.0 | | |
| 43 | 17.54 | 114.6 | | |
| 44 | 17.95 | 117.3 | | |
| 45 | 18.36 | 120.0 | | |
| 46 | 18.77 | 122.6 | | |
| 47 | 19.18 | 125.3 | | |
| 48 | 19.58 | 128.0 | | |
| 49 | 19.99 | 130.6 | | |
| 50 | 20.40 | 133.3 | | |

Figure 20:
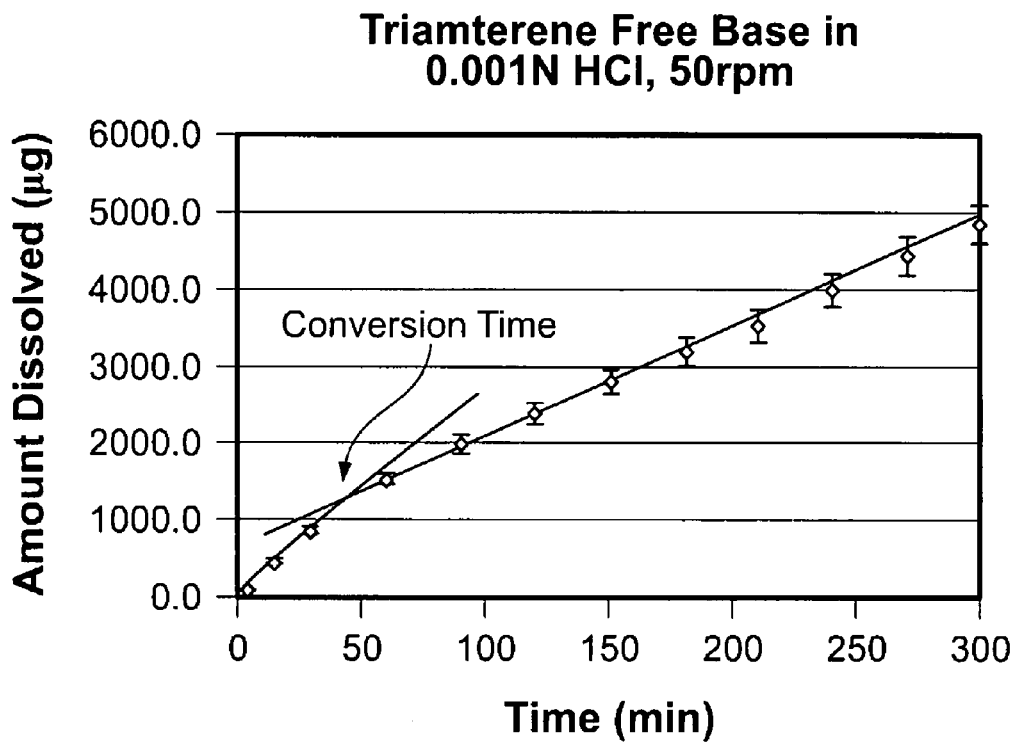
FIG. 20 is a graph illustrating Triamterene Free Base Dissolution—Cumulative Amount Dissolved vs. Time.

Dissolution data are often collected in terms of amount dissolved curve vs. time. This is the case for rotating disk experiments due to the nature of the apparatus, i.e., batch operation. In rotating disk experiments, a change in solid form (such as salt form, polymorph form, amorphous to crystalline form) is indicated by a change in slope in a cumulative dissolution curve. A change of slope signifies a change in dissolution rate. FIG. 20 shows preliminary rotating disk data for Triamterene free base dissolution in 0.001N HCl at 50 rpm. In FIG. 20, the change in slope occurs at approximately 45 minutes, although it is difficult to determine an exact time due to some curvature in the plot.

This trend has also been observed for other salt forms of other drugs. (See, e.g., Chen, L. R., et al., Dissolution Behavior of a Poorly Water Soluble Compound in the Presence of Tween 80, Pharmaceutical Research, 2003, 20(5): p. 797-801.) In the analysis done by Chen and coworkers, two straight lines were drawn on each relatively linear portion of the amount vs. time curve (similar to that shown in FIG. 20) and where these lines intersect is called the conversion time. By drawing these straight lines, it is implied that each line represents a constant dissolution rate. The conclusion of Chen and coworkers was that the conversion time signifies the beginning of nucleation and crystal growth occurs immediately and completely after nucleation.

These phenomena can be better understood by plotting a dissolution rate vs. time curve. For the rotating disk, data are still collected in a cumulative manner; however, further data treatment makes a change in slope easier to recognize. From a cumulative amount dissolved curve the slope between each set of adjacent points is taken and plotted against the midpoint of time. Using this method, it is easier to point out the time when the dissolution rate changes and determine the terminal dissolution rate. The resultant plot is a dissolution rate vs. time curve. The data from FIG. 20 are thus transformed and shown in FIG. 21.

Figure 21:
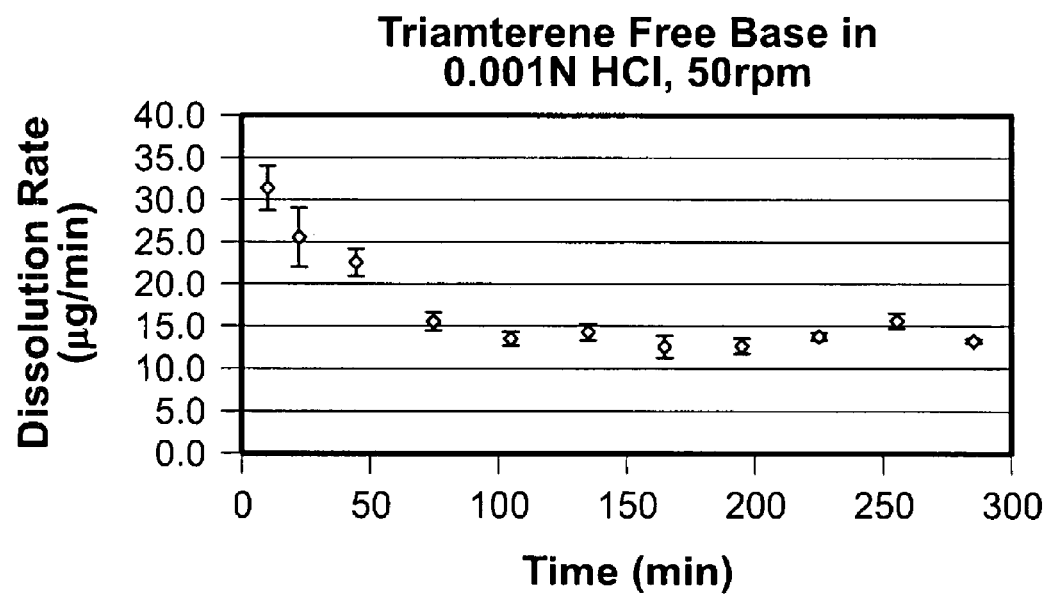
FIG. 21 is a graph illustrating Triamterene Free Base Dissolution—Dissolution Rate vs. Time.

Observing dissolution rate vs. time curve in FIG. 21, the gradual change in dissolution rate is much clearer, and it is possible to better identify a time in which the dissolution rate becomes constant. Also, it is clear that before a conversion is complete, the dissolution rate is not constant. The rate is decreasing from the start of the experiment. In addition to choosing a time in which the dissolution rate becomes constant, qualitative conclusions about the nucleation and crystal growth can be made. In FIG. 21, the nucleation of the new solid form occurs quickly after the experiment is started. This conclusion is apparent because the dissolution rate is decreasing immediately after the experiment is started. If there were a lag period before nucleation occurred, a time in which there was a constant high dissolution rate followed by a decreasing dissolution rate and then a constant lower dissolution rate would be seen. The initial decrease in dissolution rate could possibly represent the growth of a new equilibrium form on the starting solid form. Once the surface of the starting solid form is completely covered by the new solid form, the constant terminal dissolution rate can be seen.

The data in FIGS. 20 and 21 were taken from rotating disk experiments; however this data analysis technique is more straightforward using a flow-through dissolution apparatus associated with the present disclosure. In the flow-through apparatus associated with the present disclosure, it is possible to collect fractions of the outlet fluid, thus collecting the dissolution rate data directly. In the case of the flow-through apparatus, the data can be collected as fractions to fully observe the dissolution rate with time. The cumulative amount vs. time can be constructed from the fractional volume collections.

EXAMPLE 6

A flow-through apparatus associated with the present disclosure was tested using a model compound. Triamterene free base was chosen as the model compound as this is readily available and there is literature available on its various salt forms. An advantage of an apparatus associated with the present disclosure is that the user is able to observe the solid during dissolution. The following experimental results are preliminary data for a flow-through apparatus experiment (before the compression step was controlled). Approximately 20 mg of a sample drug was compressed in an insert for dissolution. Flow-through experiments were performed using 0.1N or 0.001N HCl as the dissolution medium pumped through a dissolution channel at 5 ml/min and 25 ml/min. Triamterene concentration in the effluent was measured by UV analysis at 370 nm.

Figure 22:
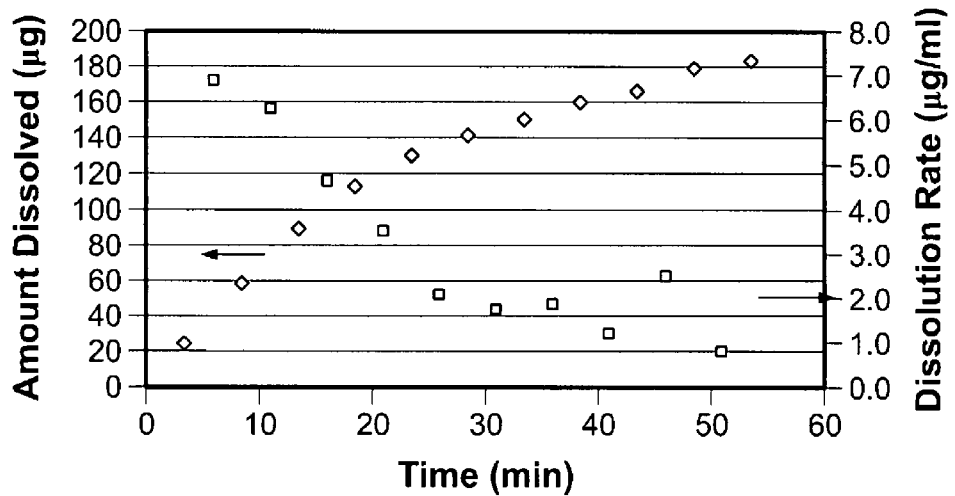
FIG. 22 is a graph illustrating amount dissolved and dissolution rate versus time of Triamterene Free Base in 0.001N HCl, 5 mL/min.

The dissolution rate of Triamterene in 0.001 HCl is not constant as shown in FIG. 22. This is evident in the amount dissolved vs. time plot, by the change in slope. This phenomenon is much more easily seen in the dissolution rate vs. time curve. For the first 25 minutes of the experiment the dissolution rate decreases. After 25 minutes, the dissolution rate appears to be relatively constant for the remainder of the experiment. Although the dissolution rate appears to be changing throughout the experiment, the images captured using a stereomicroscope did not reveal any observable changes (data not shown).

Figure 23:
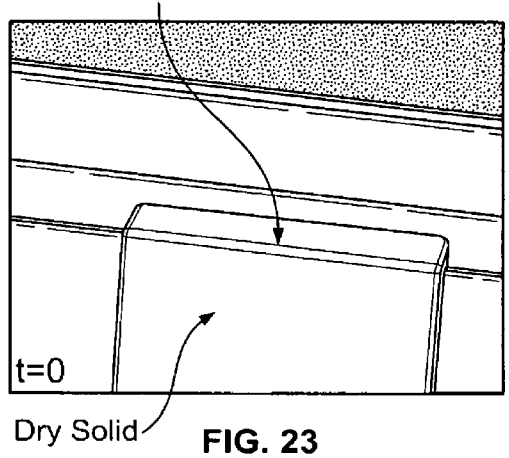
FIG. 23 illustrates dissolution at time=0 of a sample in Triamterene Free Base Dissolution in 0.1N HCl at 25 ml/min.
Figure 24:
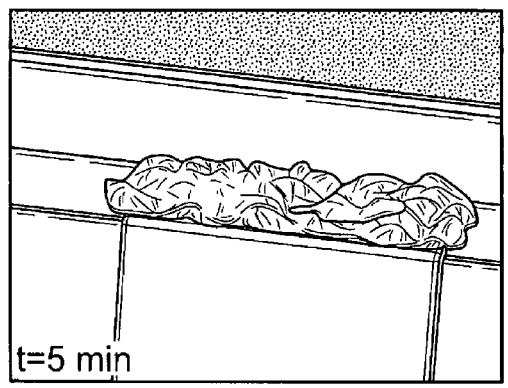
FIG. 24 illustrates dissolution at time=5 min. of a sample in Triamterene Free Base Dissolution in 0.1N HCl at 25 ml/min.
Figure 25:
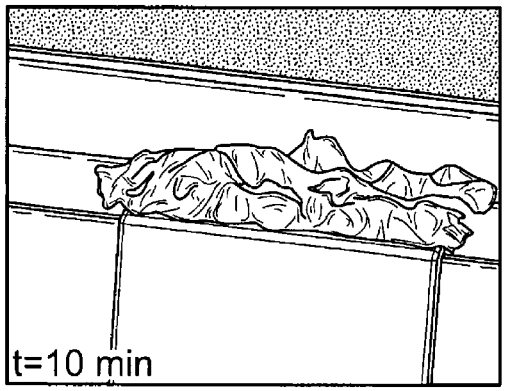
FIG. 25 illustrates dissolution at time=10 min. of a sample in Triamterene Free Base Dissolution in 0.1N HCl at 25 ml/min.
Figure 26:
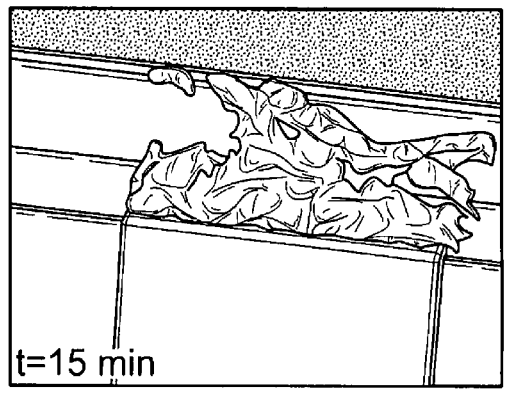
FIG. 26 illustrates dissolution at time=15 min. of a sample in Triamterene Free Base Dissolution in 0.1N HCl at 25 ml/min.
Figure 27:
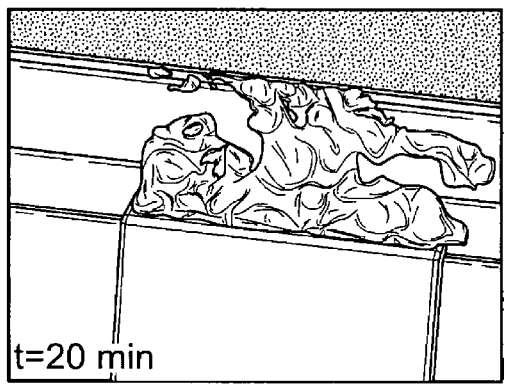
FIG. 27 illustrates dissolution at time=20 min. of a sample in Triamterene Free Base Dissolution in 0.1N HCl at 25 mL/min.
Figure 28:
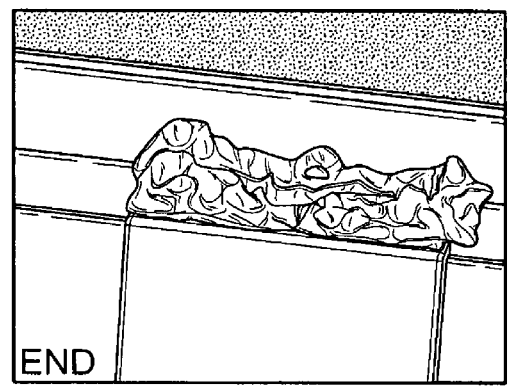
FIG. 28 illustrates dissolution at time=25 min of a sample in Triamterene Free Base Dissolution in 0.1N HCl at 25 ml/min.

Unusual results were seen in the case of the dissolution of Triamterene in 0.1N HCl at 25 ml/min. With the flow cell mounted in a jig so that it is tilted slightly, it is possible to capture images that show the face of the drug compact that is exposed to the fluid as well as the "control" dry surface face adjacent to the glass plate. Flow is from left to right in the following figures of Triamterene Free Base Dissolution in 0.1 N HCl at 25 ml/min: FIG. 23 at t=0; FIG. 24 at t=5 min; FIG. 25 at t=10 min; FIG. 26 at t=15 min; FIG. 27 at t=20 min; FIG. 28 at 25 minutes.

FIG. 23 shows the drug compact at time zero. After five minutes, it is clear that nucleation and significant crystal growth has occurred. The new solid grows significantly until 15 minutes when the new solid form is washed away with the fluid. These figures show that nucleation occurs well before the first time point. It is important to note that the concentration vs. time data collected (data not shown) for this experiment would not be valid because the surface area is drastically increasing with time. This confounds the dissolution profile of Triamterene free base in 0.1N HCl. Under these conditions, it is most likely that the HCl salt of Triamterene is forming. It has been noted that the HCl salt exhibits a "fluffy" texture.

EXAMPLE 7

In order to test an apparatus associated with the present disclosure against a rotating disk apparatus, the dissolution rate of Triamterene free base was determined in dilute NaOH. The dissolution media was chosen to be 10-4N NaOH, since at alkaline pH, the Triamterene free base is not ionized. This condition makes theoretical comparisons of flux easier since it is not necessary to account for multiple species (ionized and unionized species) and Levich's mathematical solution for dissolution from a rotating disk transport is valid.

Rotating disk dissolution was run in a standard dissolution apparatus at 25, 80 and 200 rpm. The dissolution medium was 900 ml of 10-4 N NaOH at room temperature (since the flow cell has no temperature control at this time). The Wood's die apparatus has an exposed drug surface area of 0.5 $cm^2$. Approximately 125 mg of Triamterene free base was compressed into the die using a Carver Press. The compression conditions were 5000 lbs of force for 30 seconds.

Dissolution rate was also studied in an exemplary flow-through apparatus associated with the present disclosure. The dissolution medium (10-4N NaOH) was run continuously at 0.5, 1.5, 7.0, 20 mL/min. Triamterene free base was compressed into the insert by a mini-vise. Since a pressure reading is not possible on this vise, the mass of the drug in the insert was recorded and the porosity was calculated by using the dimensions of the insert, thickness of the drug compact and true density of the Triamterene free base as measured by pycnometry. Porosity of 10% or less was considered acceptable.

Figure 29:
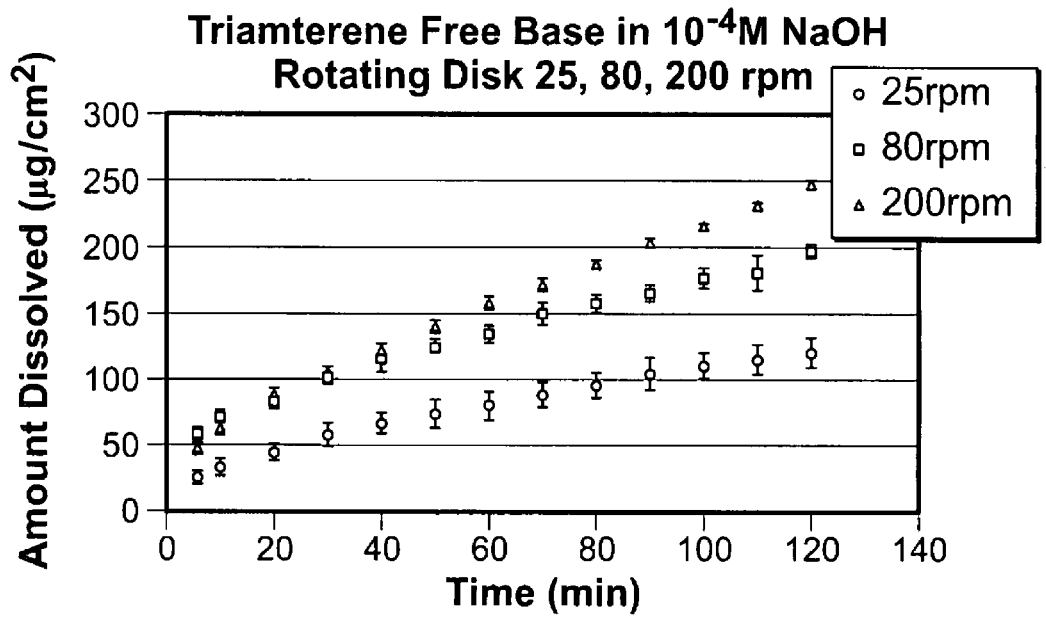
FIG. 29 is a graph illustrating Triamterene Free Base Dissolution at various rotation speeds—Cumulative Amount Dissolved vs. Time.
Figure 30:
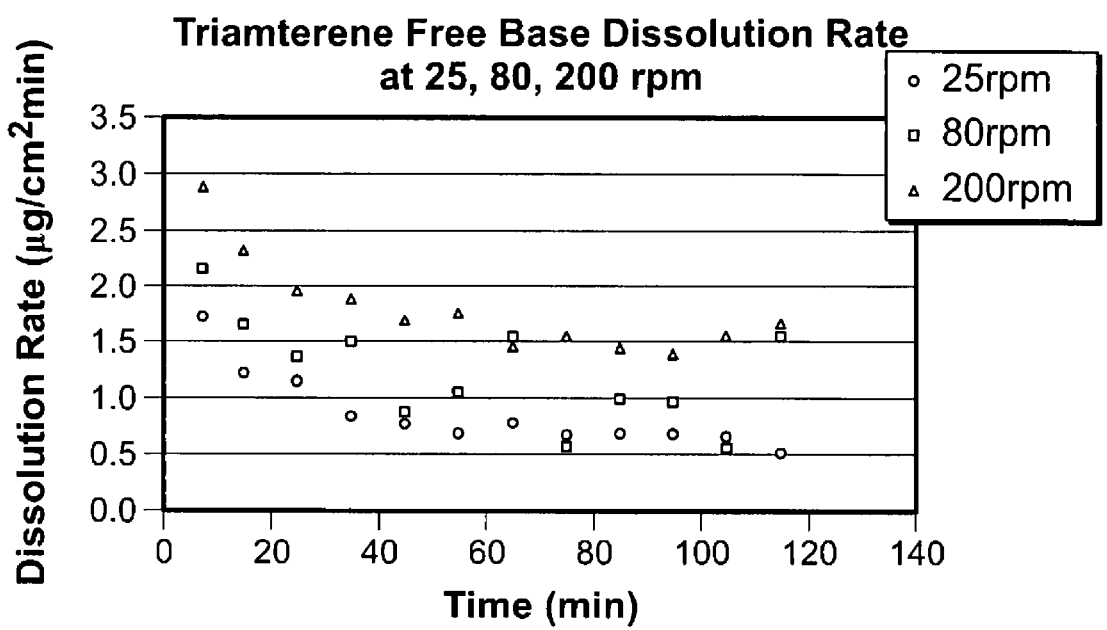
FIG. 30 is a graph illustrating Triamterene Free Base Dissolution at various rotation speeds—Dissolution Rate vs. Time.

Triamterene was detected via fluorescence with excitation at 370 nm and emission at 432 nm. The rotating disk results are shown in FIG. 29 for each rotation speed. As expected, an increase in rotation speed leads to an increase in dissolution rate. The dissolution rate for the entire experiment is represented by the slope of this line. Because this is the Triamterene free base dissolving in alkaline conditions, it is not expected to undergo a conversion, thus a constant dissolution rate vs. time curve is expected. However, interesting results can be seen in FIG. 30 showing dissolution rate vs. time data.

Although Triamterene free base is not expected to undergo a conversion in this medium, an initial decrease in the dissolution rate with time for all three rotation speeds was seen. This result is likely to obscure conversion data, although this time lag may not occur on the same time scale or with the same magnitude as a salt form conversion occurs.

Figure 31:
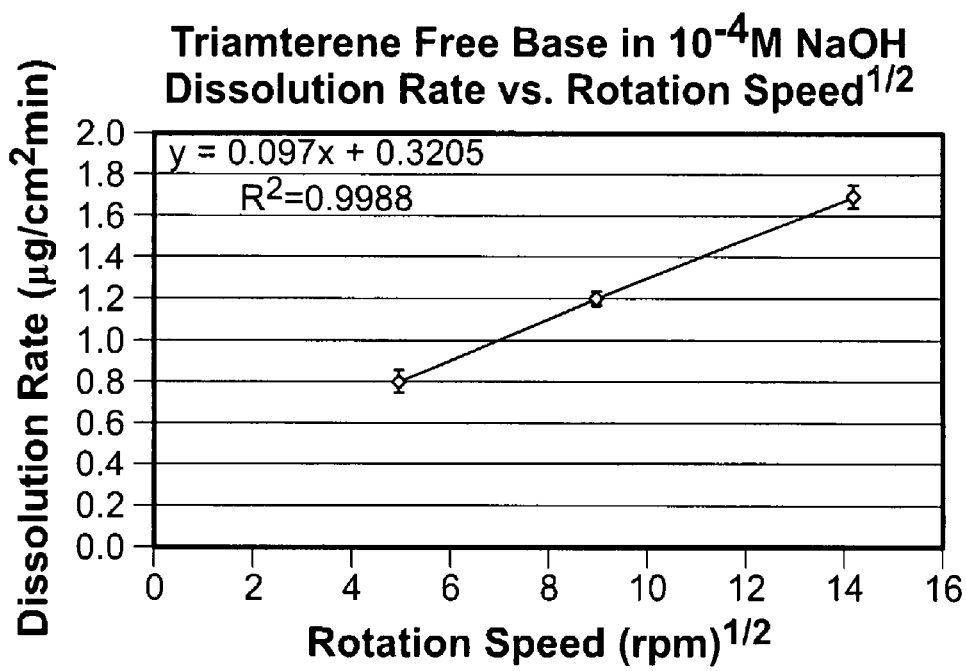
FIG. 31 is a graph illustrating Triamterene Free Base Dissolution: Dissolution Rate vs. Rotation Speed.
Figure 32:
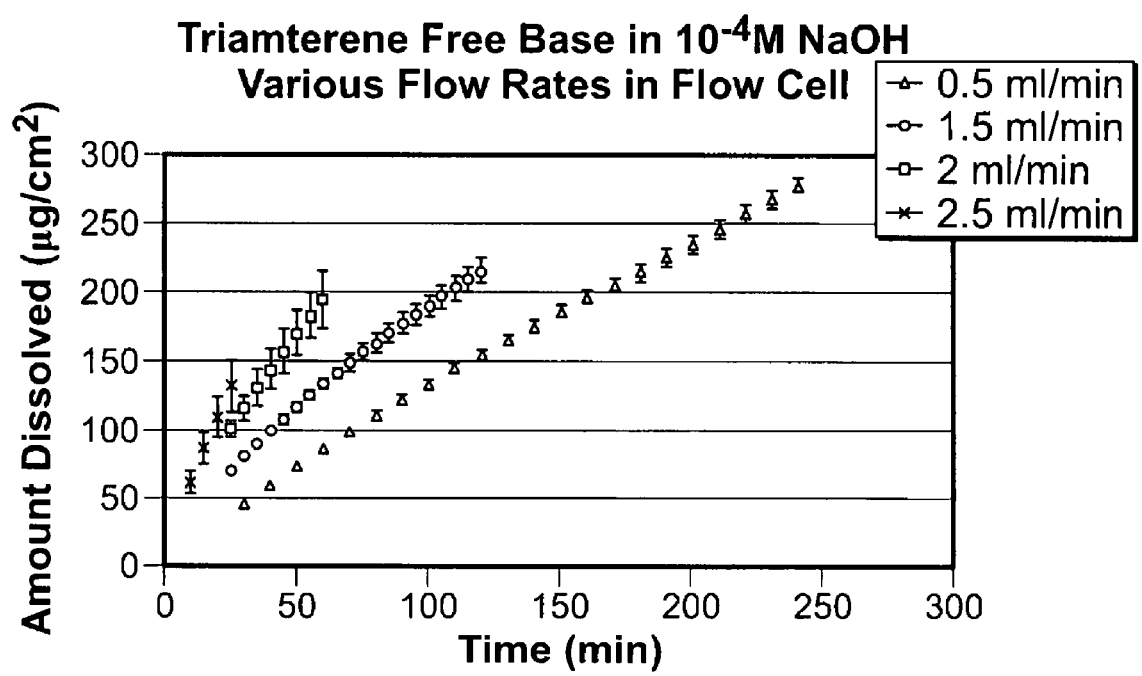
FIG. 32 is a graph illustrating Triamterene Free Base Dissolution at Various Flow Rates—Cumulative Amount Dissolved vs. Time.

As predicted from Equation 5, flux from the rotating disk is proportional to the square root of rotation speed as shown in FIG. 31. A similar set of experiments was completed for a flow-through apparatus associated with the present disclosure. The flow rates chosen were based on Equation 8. The amount dissolved vs. time data at various flow rates exhibited some curvature which implies a change in dissolution rate as shown in FIG. 32, as in the case of the rotating disk apparatus. Since the flow-through apparatus data were collected by taking volume fractions at every time point, it can easily be seen how the dissolution rate changes with time as shown in FIG. 33.

As in the case of the rotating disk, there is a decrease of dissolution rate with time. Again, this is quite unanticipated as the Triamterene free base should not convert to any other solid form under these conditions. Data for the higher flow rates (7 and 20 ml/min) were collected for only 25 and 60 minutes due to the limited fluid capacity of a syringe pump.

Figure 33:
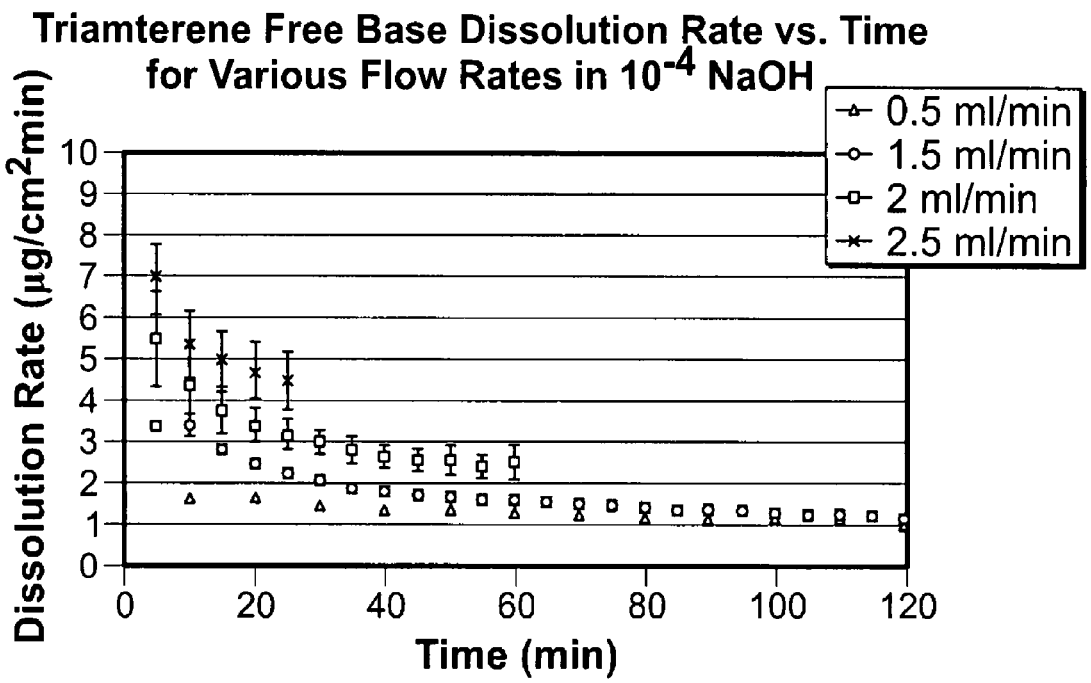
FIG. 33 is a graph illustrating Triamterene Free Base Dissolution at Various Flow Rates—Dissolution Rate vs. Time.

As shown in FIGS. 30 and 33, the dissolution rates in each apparatus were not constant as expected. The dissolution rate for Triamterene free base in the flow-through apparatus and rotating disk apparatus decreased. By observing the amount dissolved vs. time plots, it is not obvious that there is curvature in the rotating disk data. After taking the point by point derivative between points, the decrease in dissolution rate is evident. Another way to assess constancy of dissolution rate would be to plot at the residuals of the regression lines of the amount dissolved vs. time curves. For all data shown here for the rotating disk and disclosed flow cell, the residuals of the regression are non random and display a parabolic nature (data not shown). The flow-through apparatus shows a longer time lag to a constant dissolution rate. The time lag in the flow-through apparatus is longer for lower flow rates as compared to higher flow rates. Although the time lag is longer for a flow-through apparatus, one can easily observe if a conversion is occurring, unlike the rotating disk.

Figure 34:
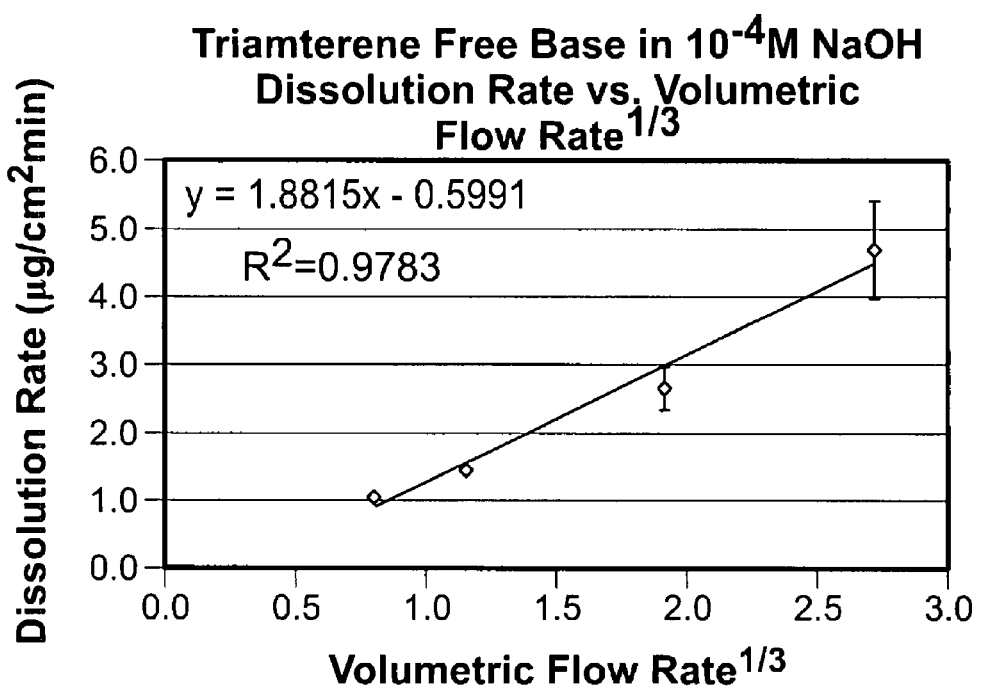
FIG. 34 is a graph illustrating Triamterene Free Base Dissolution: Dissolution Rate vs. Flow Rate.

The mass transport of a dissolving solid into a rectangular channel has been solved previously and the flux was found to be a function of the cube root of volumetric flow rate (Equation 6). The data from FIGS. 32 and 33 were used to estimate the dissolution rate at each volumetric flow rate for FIG. 34. The summary of dissolution rates in FIGS. 31 and 34 are shown in Table 6:

TABLE 6

Dissolution rates for Various Flow Rates and Rotation Speeds

| Flow Rate (ml/min) | Rotation Speed (rpm) | Dissolution Rate (ug/cm$^2$min) |
|---|---|---|
| 0.5 | | 1.1 |
| 1.5 | | 1.5 |
| 7.0 | | 2.7 |
| 20 | | 4.7 |
| | 25 | 0.8 |
| | 80 | 1.5 |
| | 200 | 2.3 |

Choosing flow rates that are comparable to rotation speeds in a Wood's die apparatus was accomplished by setting the fluxes equal in each apparatus (Equation 8), yielding 1.5 ml/min being comparable to 25 rpm, 7 ml/min to 80 rpm, and 20 ml/min to 200 rpm. The experimental flux in a flow-through apparatus is higher than expected. One possible reason for a higher dissolution rate would be caused by differences in compression of the compact between flow-through apparatus and rotating disk apparatus. When compressing solids for a flow-through apparatus, the force applied is unknown in this experimental study and only an estimate as to porosity is possible. Differences in porosity can show significant differences in dissolution rates.

An additional experiment was performed at a volumetric flow rate of 0.5 ml/min in a flow-through apparatus. By running this additional experiment, there is more overlap between the resulting fluxes in a rotating disk and a flow-through apparatus associated with the present disclosure. Therefore, it is concluded that by running the flow cell at 0.5, 1.5 and 7 ml/min fluxes similar to those found in the rotating disk at 25, 80 and 200 rpm can be achieved.

As demonstrated herein, an advantageous flow-through dissolution apparatus has been designed with the following characteristics:
1) The flow cell is small enough to fit on a microscope stage; both the dry and dissolving portions of the solid are observable, e.g., using some type of microscopy;
2) The hydrodynamics are well characterized by simulation using CFD; the surface area remains constant during dissolution; this will allow mass transport to be described using appropriate differential equations; and
3) Uses small sample size (e.g., 15 mg of a compact sample).

Exemplary uses for this apparatus include measuring dissolution rates and at the same time observing any changes in the solids visually or by a spectroscopic technique. Computational fluid dynamics simulations may be used to determine optimal channel dimensions and drug compact placement as well as optimal operating ranges for flow rates, as described herein. Shear stress may also be determined on a dissolving drug compact. These values were compared to the shear rates experienced in the USP Type II apparatus and in vivo estimations, and showed that the disclosed flow cell exhibited shear rate values similar to both USP Type II and in vivo. Theoretical comparisons between the rotating disk and flow cell apparatus were made by setting the mass flux for each apparatus equal, thus allowing estimations on comparable flow rates and rotation speeds. These comparisons will be useful in examining crystal growth on surfaces of drugs and the effect of new crystal growth according to the present disclosure.

Preliminary experiments show that the disclosed flow-through dissolution apparatus is useful in visually observing salt transformation during dissolution. Triamterene free base in 0.1N HCl at 25 ml/min showed significant hydrochloride salt growth on the drug surface during dissolution. A new approach to data analysis is also disclosed, in which the dissolution rate vs. time curve is studied. Triamterene free base dissolution was run in the rotating disk and flow cell apparatus. Using the new data analysis approach, it became clear that both experimental dissolution methods displayed a non constant dissolution rate, which is an unexpected result under these conditions which do not favor conversion. Triamterene free base dissolution rates were higher than expected in a flow cell associated with the present disclosure; however, an additional experiment was added to increase the overlap in comparable rotation speeds and flow rates. The cause for the increased dissolution rates could be due to the differences in compression between both dissolution methods. As expected, flux in the rotating disk method varied linearly with square root of rotation speed, while the flux in the flow cell varied linearly with the cube root of volumetric flow rate.

In rotating disk experiments it was found that Triamterene citrate had the highest dissolution rate in 0.01N HCl as compared to 0.1 or 0.001N HCl. This and other dissolution results using Triamterene and its salts show that solvent-mediated conversion to the HCl salt is a complex function of pH and chloride ion concentration. When chloride ion concentration was normalized to 0.1N HCl, the dissolution rate was in rank order with pH, dissolution rate is highest in 0.1N>0.01N>0.001N HCl.

Figure 35:
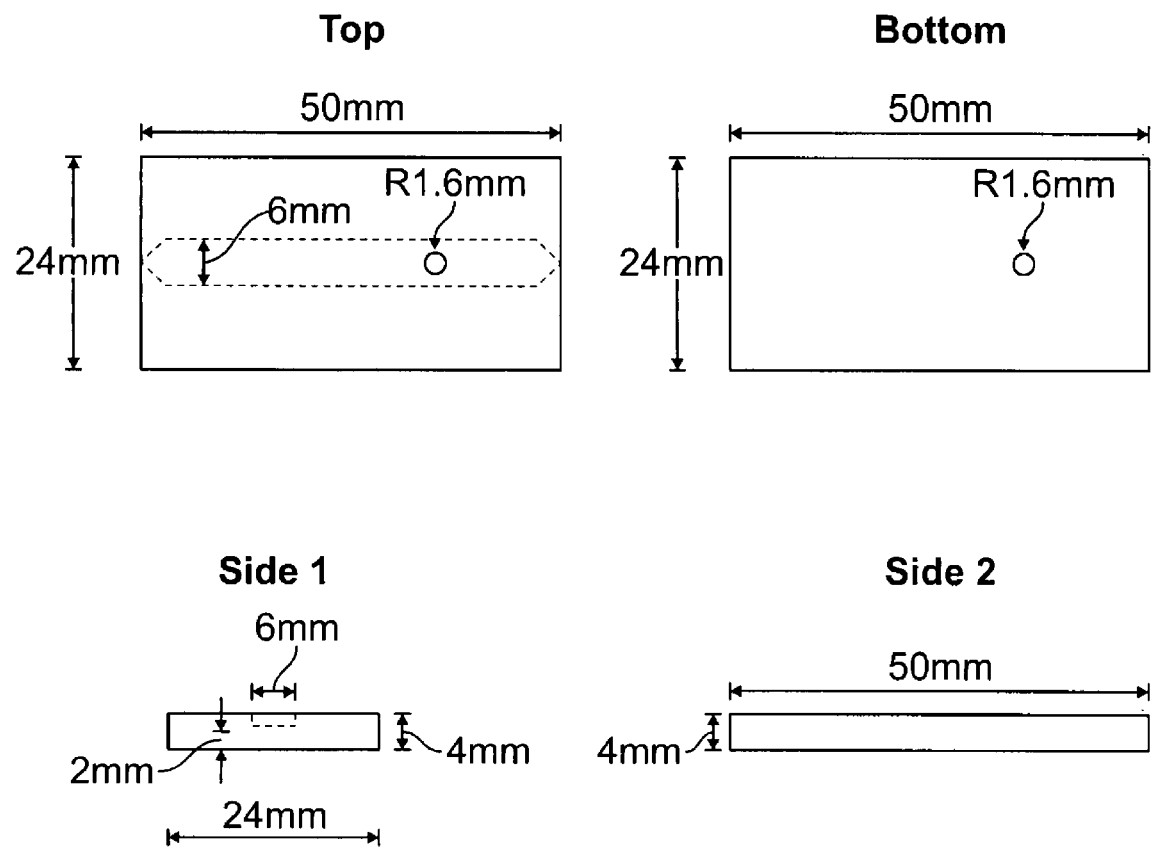
FIG. 35 illustrates an alternative geometry of an exemplary insert associated with the present disclosure.

In addition to the insert design described in the present disclosure, it is understood that many different insert designs can be used interchangeably in an exemplary dissolution flow-through apparatus. The inserts can have different channel sizes, compact sizes and views. Exemplary removable inserts use a similar outer housing as shown in FIG. 1 of the present disclosure. An example of an alternate insert design is shown in FIG. 35. An alternative exemplary insert shown in FIG. 35 illustrates an insert adapted to allow direct observation of a surface of a compact sample using a microscopy means, such as a Raman microscopy or other reflectance microscopy.

Figure 36:
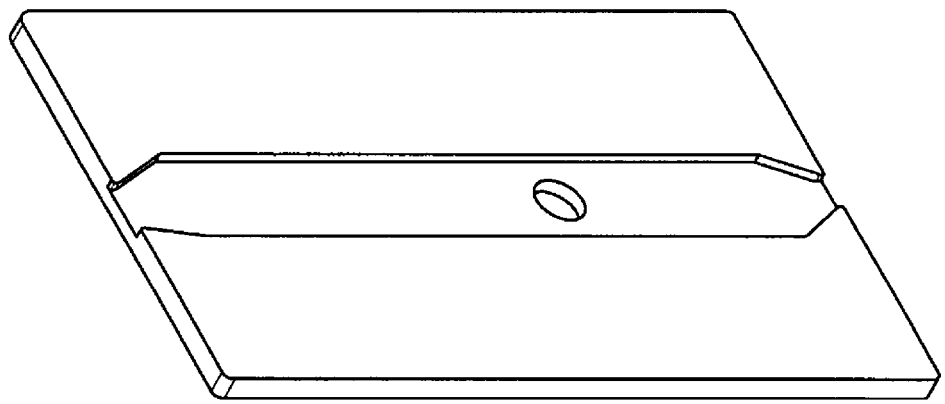
FIG. 36 illustrates an exemplary insert associated with the present disclosure defining an alternative geometry.
Figure 37:
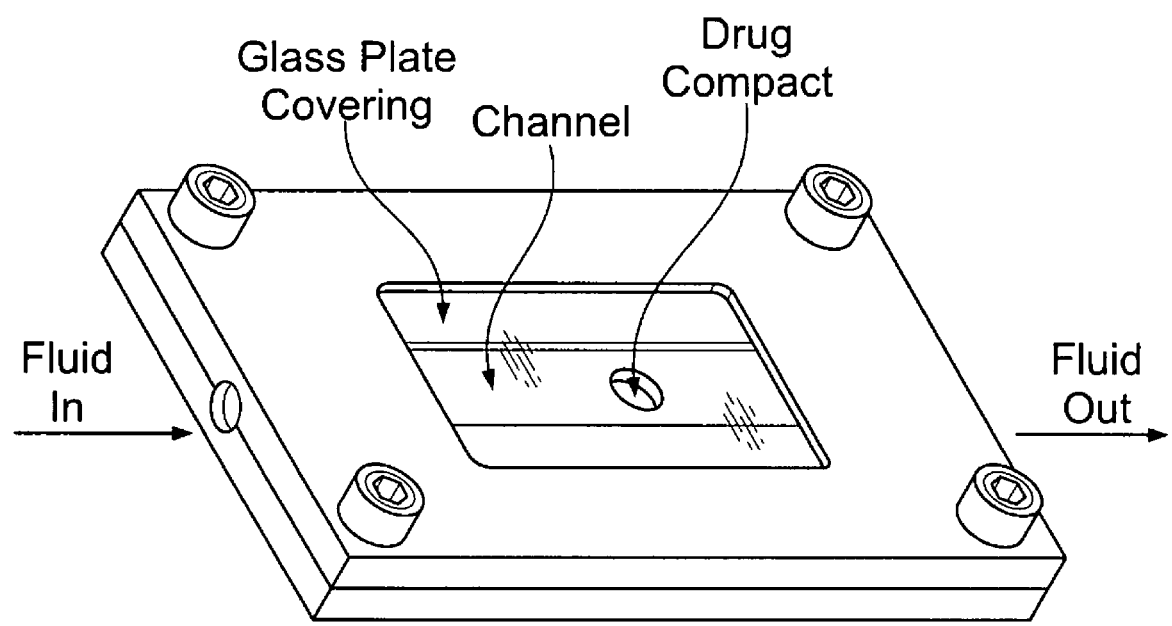
FIG. 37 illustrates an exemplary flow-through apparatus associated with the present disclosure having an alternative insert geometry as shown in FIG. 36.

An exemplary insert defining an alternative geometry to that shown in FIG. 1 is shown in FIG. 36. This exemplary insert is a single piece fabricated from stainless steel. An exemplary insert associated with FIG. 36 can be adapted to define a flow channel. In an exemplary embodiment, the dimensions of the flow channel are approximately 1×6 mm. FIG. 37 illustrates a compact sample, such as a drug sample, compacted in the channel associated with FIG. 36, such that one face of the drug compact is exposed to fluid flowing in the channel. Alternate insert designs should be adapted to allow for direct observation of the surface of the compact using Raman microscopy or other reflectance microscopy.

Exemplary inserts associated with the present disclosure can be designed to allow for direct observation and quantification of solvent-mediated transformations including: 1) metastable polymorph to stable polymorph; 2) anhydrous compound to hydrate; 3) neat amorphous solids to crystalline solids; 4) non-disintegrating amorphous formulations to crystalline dispersions; 5) salt to different salt; 6) salt to free acid or base; 7) visualization of solution conditions (e.g., pH in particular) in the solution adjacent to the dissolving solid; 8) screening of inhibitors of solvent-mediated conversion; and 9) screening a formulated solids for inhibition of solvent-mediated conversion. An apparatus such as that displayed in FIG. 7 can be used for more rapidly determining a flux versus pH profile for a new compound. The flux versus pH profile can be used to determine solubility and dissociation constant of a drug simultaneously. Using a flow-through apparatus associated with the present disclosure, the pH of a dissolution medium can be changed in a step-wise manner using a suitable apparatus to allow the flux of dissolving drug to be determined reasonably quickly.

Exemplary systems according to the present disclosure include an apparatus defining a plurality of channels. A multi-channel apparatus is adapted to allow for: (i) higher throughput testing; (ii) uniform or gradient temperature control; and/or (iii) the ability to provide a custom gradient in the dissolution medium such as a slow increase in pH over time.

An apparatus according to the present disclosure allows for improved and advantageous assaying of a dissolved sample. Typically, the dissolved sample associated with the present disclosure is dissolved in a small volume of solvent. In a typical Wood's die apparatus, the solid dissolves in a large volume of fluid, making it difficult to assay the sample early on when the concentration of the dissolved sample is below the limit of quantification.

Although the advantageous systems, methods and apparatus have been described with reference to exemplary embodiments, the present disclosure is not limited thereto. Rather, many modifications, variations and/or enhancements may be made without departing from the spirit or scope of the present disclosure.

What is claimed:

1. A flow-through apparatus comprising:
   a frame including a transparent surface; and
   a removable insert defining a cavity for receiving a compacted sample;
   wherein the insert is adapted to fit within the frame and cooperate therewith to define at least one flow-through channel for laminar fluid flow through the frame;
   wherein, the flow-through apparatus is configured such that when the compacted sample is received within the cavity of the insert fitted within the frame, a first surface of the compacted sample partially defines the flow-through channel and is exposable to laminar fluid flow, and a second surface of the compacted sample, perpendicular to the first surface at an interface, is directly adjacent to the transparent surface of the frame and is isolated from fluid flow;
   wherein at least part of the interface between the first surface and second surface of the compacted sample is directly adjacent to both the flow through channel and the transparent surface of the frame such that the interface is at least partially externally visible through the transparent surface of the frame.

2. The apparatus according to claim 1, wherein the transparent surface of the frame includes a glass plate.

3. The apparatus according to claim 1, wherein the frame includes a top portion and a bottom portion adapted to securely fit together around the insert.

4. The apparatus according to claim 1, wherein the sample is compacted within the cavity of the insert.

5. The apparatus according to claim 4, wherein the amount of sample compacted into the insert is less than or equal to 50 mg.

6. The apparatus according to claim 5, wherein the amount of compact sample compacted into the insert is less than or equal to 15 mg.

7. The apparatus according to claim 1, wherein the sample is a solid sample that dissolves during interaction with a fluid.

8. The apparatus according to claim 7, wherein the solid sample is a pharmaceutical solid sample.

9. The apparatus according to claim 1, wherein the frame defines a substantially rectangular geometry and the flow-through channel is defined along the elongated axis of the frame.

10. The apparatus according to claim 9, wherein the dimensions of the frame are approximately 75 mm in length, 40 mm in width, and 1.5 cm in height.

11. The apparatus according to claim 1, wherein the insert defines a substantially rectangular geometry.

12. The apparatus according to claim 1, wherein the compacted sample defines a substantially three-dimensional rectangular shape defining dimensions of approximately 2 mm in height, 4 mm in width, and 1-2 mm in thickness.

13. The apparatus according to claim 1, wherein a cross section of the flow-through channel defines a substantially rectangular geometry.

14. The apparatus according to claim 1, wherein the compacted sample defines three surfaces which are externally visible through the transparent surface of the frame.

15. The apparatus according to claim 1, wherein the apparatus is configured such that exposure of the first surface of the compacted sample to the laminar fluid flow is observable through a microscopy means.

16. The apparatus according to claim 1, wherein the transparent surface of the frame further includes a second glass plate positioned to space the first surface of the compacted sample away from a corner of the flow-through channel.

17. The apparatus according to claim 1, wherein the glass plate is a microscope coverslip of appropriate dimensions so that it securely fits within the frame and is adapted to cover the sample and the flow-through channel.

18. The apparatus according to claim 1, wherein the frame is dimensioned to fit on a microscope stage.

19. The apparatus according to claim 1, wherein the frame is fabricated from stainless steel.

20. The apparatus according to claim 1, wherein the insert is fabricated from stainless steel.

21. The apparatus according to claim 1, wherein fluid is pumped through the flow channel by a fluid delivery means.

22. The apparatus according to claim 21, wherein the fluid delivery means is a syringe pump.

23. The apparatus according to claim 1, wherein the hydrodynamic characteristics of the laminar fluid flow through the flow-through channel are known or computed.

24. The apparatus according to claim 1, wherein the frame defines a plurality of flow channels.

25. The apparatus according to claim 24, wherein the frame is operable to allow for high throughput testing.

26. The apparatus according to claim 24, wherein the frame is operable to allow for uniform or gradient temperature control through at least one of the flow channels.

27. The apparatus according to claim 24, wherein the frame is operable to allow for the ability to provide a custom gradient in the dissolution medium.

* * * * *